US011844820B2

(12) United States Patent
McKay et al.

(10) Patent No.: US 11,844,820 B2
(45) Date of Patent: Dec. 19, 2023

(54) TOPICAL FORMULATION AND USES THEREOF

(71) Applicant: ARTHRITIS RELIEF PLUS LTD., Bundall (AU)

(72) Inventors: Larry McKay, Montville, NJ (US); Kanu Patel, Londonderry, NH (US); Robert John Capon, Pullenvale (AU)

(73) Assignee: ARTHRITIS RELIEF PLUS LTD., Brisbane (AU)

( * ) Notice: Subject to any disclaimer, the term of this patent is extended or adjusted under 35 U.S.C. 154(b) by 0 days.

(21) Appl. No.: 16/397,220

(22) Filed: Apr. 29, 2019

(65) Prior Publication Data

US 2019/0255133 A1 Aug. 22, 2019

Related U.S. Application Data

(63) Continuation of application No. 12/515,254, filed as application No. PCT/AU2007/001753 on Nov. 15, 2007, now Pat. No. 10,322,155.

(60) Provisional application No. 60/981,077, filed on Oct. 18, 2007, provisional application No. 60/866,001, filed on Nov. 15, 2006.

(51) Int. Cl.
| | |
|---|---|
| *A61K 36/30* | (2006.01) |
| *A61K 36/00* | (2006.01) |
| *A61K 45/06* | (2006.01) |
| *A61K 31/14* | (2006.01) |
| *A61K 31/198* | (2006.01) |
| *A61K 31/4166* | (2006.01) |

(52) U.S. Cl.
CPC ............ *A61K 36/30* (2013.01); *A61K 31/14* (2013.01); *A61K 31/198* (2013.01); *A61K 31/4166* (2013.01); *A61K 36/00* (2013.01); *A61K 45/06* (2013.01)

(58) Field of Classification Search
CPC ...... A61K 36/30; A61K 31/14; A61K 31/198; A61K 31/4166; A61K 36/00; A61K 45/06; A61P 19/00; A61P 19/06; A61P 29/02; A61P 19/02; A61P 29/00
See application file for complete search history.

(56) References Cited

U.S. PATENT DOCUMENTS

| | | | |
|---|---|---|---|
| 3,903,307 A | 9/1975 | Kimura | |
| 4,381,296 A | 4/1983 | Tinnell | |
| 4,670,263 A | 6/1987 | Noorlander | |
| 5,028,429 A | 7/1991 | Gochenouer | |
| 5,286,488 A | 2/1994 | Manikas et al. | |
| 5,958,418 A | 9/1999 | Prillerman | |
| 5,962,018 A * | 10/1999 | Curtis | A61K 9/1635 424/450 |
| 6,071,962 A * | 6/2000 | Ptchelintsev | A61K 31/195 514/558 |
| 6,656,229 B1 | 12/2003 | Taguchi et al. | |
| 7,678,768 B2 | 3/2010 | Purpura et al. | |
| 2004/0033246 A1 | 2/2004 | Naru et al. | |
| 2004/0131704 A1 | 7/2004 | Morse | |
| 2007/0185348 A1 | 8/2007 | Appeldoorn et al. | |
| 2009/0005322 A1 | 1/2009 | Purpura et al. | |
| 2009/0081285 A1 | 3/2009 | Golz-Berner et al. | |

FOREIGN PATENT DOCUMENTS

| | | |
|---|---|---|
| AU | 2005266505 B2 | 2/2006 |
| CN | 1398869 A | 2/2003 |
| CZ | 277721 B6 * | 3/1993 |
| EP | 1 647 282 A1 | 4/2006 |
| JP | 07-278001 | 10/1995 |
| JP | 08-208451 | 8/1996 |
| JP | 2000-236848 A | 9/2000 |
| JP | 2001-064155 | 3/2001 |
| JP | 2002-179547 | 6/2002 |
| JP | 2002-255803 | 9/2002 |
| JP | 2004-307456 A | 11/2004 |
| JP | 2006-036675 A | 2/2006 |
| RO | 113711 B | 10/1998 |
| RU | 2044547 | 9/1995 |
| WO | WO 02/41832 A2 | 5/2002 |
| WO | WO 2004/045380 A1 | 6/2004 |
| WO | WO 2006/010606 A1 | 2/2006 |
| WO | WO 2006/117404 A2 | 11/2006 |

OTHER PUBLICATIONS

Venu "How to Treat Arthritis with a Comfrey Poultice", FindArthritistreatment.com, Sep. 29, 2012. [Retrived from the internet Dec. 19, 2016, <URL:https://web.archive.org/web/20120929002717/http://www.findarthritistreatment.com/how-to-treat-arthritis-with-a-comfrey-poultice>, 6 pages. (Year: 2012).*
Anonymous, "The use of Tannic Acid in the Local Treatment of Burn Wounds: Intriguing Old and New Perspectives", Wounds, vol. 13, No. 4 (2001) retrieved from internet http://www.medscape.com/viewarticle/407583_print.
Bonnet et al., "Osteoarthritis, angiogenesis and inflammation", Rheumatology, vol. 44 (2005) pp. 7-16.
European Office Action issued in European Patent Application No. 07 815 556.1 dated Aug. 5, 2015.
Japanese Office Action issued in Japanese Patent Application No. 2009-536560 dated Feb. 4, 2014.

(Continued)

*Primary Examiner* — Aaron J Kosar
(74) *Attorney, Agent, or Firm* — Birch, Stewart, Kolasch & Birch, LLP

(57) ABSTRACT

The present invention provides a topical formulation including (i) comfrey or a comfrey-derived compound, or an analogue or derivative thereof and (ii) a penetration enhancer, and optionally including tannic acid, or an analogue or derivative thereof. The present invention also provides a topical formulation including (i) comfrey or a comfrey-derived compound, or an analogue or derivative thereof, and (ii) tannic acid, or an analogue or derivative thereof, optionally including a penetration enhancer. Also provided are kits and methods of prophylactic or therapeutic treatment of inflammatory and/or degenerative conditions using the combination of active ingredients as herein described.

4 Claims, No Drawings

(56) References Cited

OTHER PUBLICATIONS

Lee et al., "Inhibition of Inducible Nitric Oxide Synthase and Cyclooxygenase-2 Activity by 1,2,3,4,6-Penta-O-galloyl-β-D-glucose in Murine Macrophage Cells", Arch Pharm Res, vol. 26, No. 10 (2003) pp. 832-839.

Mrowietz et al., "Selective Inactivation of Human Neutrophil Elastase by Synthetic Tannin", Journal of Investigative Dermatology, vol. 97, No. 3 (1991) pp. 529-533.

Srivastava et al., "Green tea polyphenols and tannic acid act as potent inhibitors of phorbol ester-induced nitric oxide generation in rat hepatocytes independent of their antioxidant properties", Cancer Letters, vol. 153 (2000) pp. 1-5.

Translation of Office Action dated Nov. 8, 2012 in corresponding Japanese Application JP 2009-536560.

Chin, L., et al., "Lead chelation to immobilised *Symphytum officinale* L. (comfrey) root tannins," Chemosphere, vol. 76, pp. 711-715 (2009).

EP Search Report for Application No. EP 07 81 5556.1.

European Search Report issued in European Patent Application No. 07815556.1 dated Apr. 13, 2010.

Grube et al., "Efficacy of a comfrey root (Symphyti offic. radix) extract ointment in the treatment of patients with painful osteoarthritis of the knee: Results of a double-blind, radomised, bicenter, placebo-controlled trial", Phytomedicine, vol. 14 (2007) pp. 2-10.

Koll, R., et al., "Efficacy and tolerance of a comfrey root extract (Extr. Rad. Symphyti) In the treatment of ankle distorsions: results of a multicenter, randomized, placebo-controlled, double-blind study," Phytomedicine, vol. 11, pp. 470-477 (2004).

Kucera, M., et al., "Topical symphytum herb concentrate cream against myalgia: a randomized controlled double-blind clinical study," Adv. Ther., vol. 22, No. 6, pp. 681-692 (2005) (with English Abstract).

Predel, H.-G., et al., "Efficacy of a Comfrey root extract ointment in comparison to a Diclofenac gel in the treatment of ankle distortions: Results of an observer-blind, randomized, multicenter study," Phytomedicine, vol. 12, pp. 707-714 (2005).

Sanchez-Moreno et al. Free Radical Scavenging Capacity and Inhibition of Lipid Oxidation of Wines, Grape Juices and Related Polyphenolic Constituents; Food Research International 32 (1999) 407-412.

Treben, M. "Arthritis: Comfrey Root Tincture" from "Health from God's Garden: Herbal Remedies for Glowing Health and Well-Being". 1986. p. 85.

XP-002572639—Staiger, C., "Beinwell bei akuten Sprungelenkdistorsionen," Phytotherapie, No. 3, pp. 28-30 (2006).

\* cited by examiner

TOPICAL FORMULATION AND USES THEREOF

CROSS REFERENCE TO RELATED APPLICATIONS

This application is a continuation of copending U.S. patent application Ser. No. 12/515,254, filed Jul. 20, 2009, which is a National Phase Under 35 U.S.C. § 371 of International Application No. PCT/AU2007/001753 which has an International filing date of Nov. 15, 2007, which claims priority under 35 USC § 119(e) to US Provisional Application No. 60/866,001 filed on Nov. 15, 2006 and US Provisional Application No. 60/981,077 filed on Oct. 18, 2007. The entire contents of all applications listed above are hereby incorporated by reference.

The present invention relates generally to a topical formulation and its use in the treatment or prevention of degenerative and/or inflammatory conditions.

BACKGROUND

Whilst the present invention has application in the treatment and prevention of many forms of degenerative and/or inflammatory conditions, for the purpose of brevity, the following description shall be limited to discussing its application in the treatment of arthritis, although it should be appreciated that the formulations of the invention could be used to treat other degenerative and/or inflammatory conditions.

Arthritis is a degenerative condition of a joint or joints that is generally associated with pain and inflammation. The two most common forms of arthritis are osteoarthritis and rheumatoid arthritis. Osteoarthritis (OA) is a progressive rheumatic disease characterized by the degeneration of articular cartilage. It is the most common of all rheumatic disorders and is destined to become one of the most prevalent and costly diseases in Western society.

Therapeutic interventions conventionally employed for OA include the use of physiotherapy and antidepressant therapies, patient education and weight control. In addition, drug therapy includes non-opioid analgesics such as paracetamol, non-steroidal anti-inflammatory drugs (NSAIDs), topical analgesics, COX-2 inhibitors, opioid analgesics and intra-articular steroid injection. However, such treatments often prove ineffective in some patients and NSAIDS can have serious adverse effects. For instance, gastrointestinal complications are frequently reported with NSAIDs, with approximately 12,000 hospitalizations and about 2000 deaths attributed to NSAID use in the UK every year. Hence there appears to be a need for drugs with good efficacy and low toxicity in the treatment of OA. Specifically, there is a need for safe and effective drugs for patients who do not respond well to conventional medical therapy. In this respect, many patients are turning increasingly to complementary/alternative medicines (CAM).

The use of CAM by sufferers of rheumatic diseases is highly prevalent and increasing. Arthritis is the sixth most frequently cited health problem treated with CAM in the USA. Individuals who use CAM regularly are more likely to have OA and severe pain. Patients suffering from musculoskeletal problems are likely to be users of herbal treatments. It is therefore important to determine the effectiveness and safety of herbal medicines in the treatment of OA.

A review by Long et al. (*Rheumatology*, 2001, 40:779-793) found promising evidence in the form of randomized controlled trials of herbal medicines and plant extracts in reducing pain and improving mobility, function and disability in OA. While there is no compelling evidence for significant clinically relevant benefits for CAMs such as Eazmov, Gitadyl or ginger extract, there is weak evidence, in the form of single randomized controlled trials, for mild to moderate relief of symptoms using Reumalex, willow bark, common stinging nettle and the Ayurvedic herbal preparation, Articulin-F. There is also promising evidence for the efficacy of devil's claw and extracts of avocado and soya bean, as well as moderately strong evidence for the efficacy of Phytodolor and capsaicin cream for the relief of OA symptoms.

Topically applied capsaicin is also proposed to exert its action by stimulating a subpopulation of nociceptive pain neurones. Exposure to capsaicin brings about the depletion of substance P, neurones subsequently becoming insensitive to all other exposure, including exposure to capsaicin itself.

The incidence of adverse effects for these herbal medicines appears to be low, and they may offer a much-needed alternative for individuals with long-term chronic OA.

Comfrey root or leaf (in either a crude form or as an extract thereof) has been used in the treatment of OA, however, formulations that include comfrey extracts have only been used to provide temporary relief for the pain associated with OA. For instance, U.S. Pat. No. 5,958,418 describes a herbal composition for the treatment of muscular aches and pains, the composition comprising Aloe vera, capsicum, Golden Seal, the finely chopped bark of the comfrey root and water. U.S. Pat. No. 6,333,056 describes an ingestible herbal based formulation for treatment of horses and dogs to alleviate the symptoms of osteoarthritis, the formulation comprising a mixture of devils claw and comfrey (in a certain embodiment, it may also include a mixture of dandelion, burdock and nettles), as an intimate admixture added to the animals' feed. U.S. Pat. No. 4,059,695 describes a tonic composition in liquid form comprising refined wood vinegar and plant leaf components, such as comfrey leaf, that is said to mitigate arthritis, although experimental evidence is not provided to support that assertion.

The present invention overcomes, or at least alleviates, some of the aforementioned problems of the art by providing a more effective prophylactic or therapeutic treatment for inflammatory and/or degenerative conditions and topical formulations for such use.

The discussion of documents, acts, materials, devices, articles and the like is included in this specification solely for the purpose of providing a context for the present invention. It is not suggested or represented that any or all of these matters formed part of the prior art base or were common general knowledge in the field relevant to the present invention as it existed before the priority date of each claim of this application.

SUMMARY OF THE INVENTION

In a first aspect, the present invention provides a topical formulation including (i) comfrey or a comfrey-derived compound, or an analogue or derivative thereof, and (ii) a penetration enhancer. Comfrey may be a crude comfrey leaf or root product, comfrey root or leaf extracts, or any combination thereof. A comfrey-derived compound can be any compound that is normally found in comfrey and includes, but is not limited to, allantoin, choline, asparagine, phenolic acid (e.g., rosemarinic acid, chlorogenic acid, caffeic acid and lithospermic acid), rosmaric acid, volatile oil, tannin, a steroidal saponin, a triterpene and vitamin B12.

Whilst the amount of comfrey or comfrey-derived compound in the topical formulation of the present invention may be altered by a skilled person to suit a particular use, in one embodiment it is present in an amount that is from about 0.5% to about 40% of the total weight of the topical formulation.

In another aspect of the present invention, the topical formulation may also include tannic acid, or an analogue or derivative thereof. Tannic acid (or the analogue or derivative thereof) may be in the form of a crude plant extract (e.g., a nutgall extract) or as a substantially pure pharmaceutical grade. Whilst the amount of tannic acid (or the analogue or derivative thereof) used in the topical formulation of the present invention can be altered by a skilled person to suit a particular use, it may be present in an amount that is from about 2% to about 20% of the total weight of the topical formulation.

The penetration enhancer used in the topical formulation of the present invention may be selected from the group consisting of borage oil, eucalyptus oil (such as eucalyptus globulus oil) and tetrahydropiperine (such as cosmoperine), or combinations thereof. Whilst the amount of penetration enhancer used in the topical formulation of the present invention can be altered by a skilled person to suit a particular use, in one embodiment it is present in an amount that is at least 0.05% of the total weight of the topical formulation. In one embodiment, the penetration enhancer is eucalyptus globulus oil. Eucalyptus globulus (synonym: blue gum) is a tree of the family Myrtaceae. Eucalyptus globulus oil (also known as eucalyptus aetheroleum) constitutes approximately 0.45% to 1.65% of fresh leaf matter. The oil contains terpene 1,8-cineol (80-90%), p-cymene, a-pinene, limonene, gerianol, camphene and euglobals. The leaf wax also contains flavanoids such as quercetin, quercitrin and rutoside as well as methylflavone eucalyptin. Eucalyptus globulus may be prepared by any methods known to the skilled artisan, including, but not limited to, ethanolic extraction and/or steam distillation of the twigs or of the fresh or dried leaves.

In yet another aspect, the present invention provides a topical formulation including (i) comfrey or a comfrey-derived compound, or an analogue or derivative thereof, as herein described, and (ii) tannic acid, or an analogue or derivative thereof, as herein described. Whilst the amount of tannic acid used in the topical formulation of the present invention can be altered by a skilled person to suit a particular use, it may be present in an amount that is from about 2% to about 20% of the total weight of the topical formulation.

In one embodiment of the present invention, the topical formulation may also include a penetration enhancer including, but not limited to, borage oil, eucalyptus oil (such as eucalyptus globulus oil) and tetrahydropiperine (such as cosmoperine), or combinations thereof, as herein described.

It has been found that the formulations of the present invention provide prolonged relief from inflammatory and/or degenerative conditions and the pain, swelling, stiffness and/or lack of mobility associated with said inflammatory and/or degenerative conditions.

In another aspect of the present invention, there is provided a method for the prophylactic or therapeutic treatment of an inflammatory and/or degenerative condition, wherein the method includes applying a topical formulation including (i) comfrey or a comfrey-derived compound, or an analogue or derivative thereof, and (ii) a penetration enhancer to a subject in need thereof and to an area affected by inflammation and/or degeneration or to an area expected of becoming affected by inflammation and/or degeneration, and optionally applying tannic acid to that area.

In yet another aspect of the present invention, there is provided a method for the prophylactic or therapeutic treatment of an inflammatory and/or degenerative condition, wherein the method includes applying a topical formulation including (i) comfrey or a comfrey-derived compound, or an analogue or derivative thereof, and (ii) tannic acid, or an analogue or derivative thereof, to a subject in need thereof and to an area affected by inflammation and/or degeneration or to an area expected of becoming affected by inflammation and/or degeneration, and optionally applying a penetration enhancer to that area.

There is also provided a use of a topical formulation, as herein described, in the manufacture of a medicament for the prophylactic or therapeutic treatment of an inflammatory and/or degenerative condition, wherein the treatment includes applying an amount of said topical formulation to a subject in need thereof and to an area affected by inflammation and/or degeneration or to an area expected of becoming affected by inflammation and/or degeneration.

Types of inflammatory and/or degenerative conditions applicable to the methods and uses according to the present invention include, but are not limited to, osteoarthritis, rheumatoid arthritis, septic arthritis, gout, pseudogout, juvenile arthritis, Still's disease, cervical spondylitis, lumbar spondylitis, frozen shoulder, calcaneal spurs, psoriatic arthritis and ankylosing spondylitis.

In another aspect of the present invention, there is provided a kit including a first container that includes a penetration enhancer, as herein described, and a second container including comfrey, or a comfrey-derived compound, or an analogue or derivative thereof, as herein described. The kit may optionally include a third container including tannic acid, or an analogue or derivative thereof, as herein described. There is also provided a kit including a first container that includes comfrey or a comfrey-derived compound, or an analogue or derivative thereof, as herein described, and a second container including tannic acid, or an analogue or derivative thereof, as herein described. The kit may optionally include a third container including a penetration enhancer, as herein described. There is provided a kit including a container having a topical formulation according to the present invention, as herein described.

DETAILED DESCRIPTION OF THE PRESENT INVENTION

In a first aspect, the present invention provides a topical formulation including (i) comfrey or a comfrey-derived compound, or an analogue or derivative thereof, and (ii) a penetration enhancer.

Comfrey is a perennial herb of the family Boraginaceae with a black, turnip-like root and large, hairy broad leaves that bears small bell-shaped white, cream, purple or pink flowers. It is native to Europe, growing in damp, grassy places, and is widespread throughout the British Isles on river banks and ditches. Comfrey has long been recognised by both organic gardeners and herbalists for its great usefulness and versatility. Comfrey has been used to treat a wide variety of ailments ranging from bronchial problems, broken bones, and gastric and varicose ulcers.

The comfrey may be a crude comfrey leaf or root product, a comfrey root or leaf extract or any combination thereof. Whilst the amount of comfrey in the topical formulation of the present invention may be altered by a skilled person to suit a particular use, it has been found that an amount that is at least 0.5% of the total weight of the topical formulation has particular beneficial properties in alleviating pain and discomfort associated with inflammatory and/or degenerative conditions, such as arthritis. In another embodiment of the present invention, the amount of comfrey will be in the range of from about 0.5% to about 40% of the total weight of the topical formulation of the present invention.

Comfrey-derived compounds include, but not limited to, allantoin, choline, asparagine, phenolic acid (e.g., rosemarinic acid, chlorogenic acid, caffeic acid and lithospermic acid), rosmaric acid, volatile oil, tannin, a steroidal saponin, a triterpene and vitamin B12. In one embodiment, a comfrey-derived compound may be a naturally-occurring compound that is extracted by methods known to those skilled in the art, and optionally at least partially purified as required. In one embodiment, the comfrey-derived compound is purified to a substantially pure form as required. The term "substantially pure", as used herein, typically means a compound which is substantially free of other compounds with which it may normally be associated in vivo.

Importantly, a comfrey-derived compound, as used herein, is not intended to limit the present invention to the compounds derived by methods of, for example, extraction from comfrey or an extract thereof. Thus, in another embodiment of the present invention, the comfrey-derived compound may be synthetic, manufactured by processes known to those skilled in the art. Combinations of naturally-occurring and synthetic compounds are also envisaged in certain embodiments of the present invention.

In one embodiment of the present invention, the comfrey-derived compound is allantoin, or an analogue or derivative thereof. Allantoin is an oxidative product of uric acid:

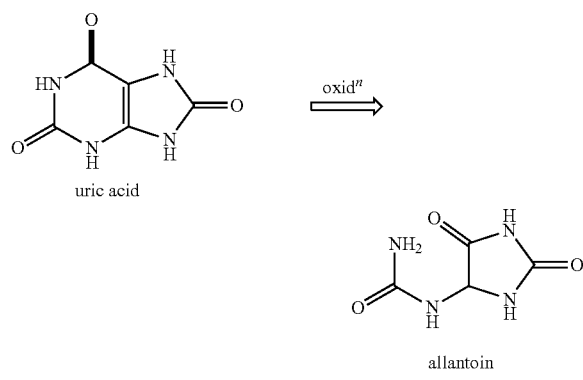

In a certain embodiment of the present invention, the allantoin derivative has the following chemical structure, allowing for all stereoisomers thereof in pure, mixed or racemic form:

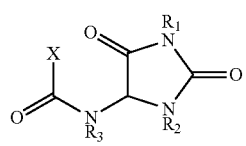

wherein:

$R_1$, $R_2$ and $R_3$ are each independently H, alkyl, alkenyl, alkynyl, acyl or aryl; and X=OH, $OR_1$, $NH_2$, $NHR_1$ or $NR_1R_2$. In a further embodiment, $R_1$ $R_2$ and $R_3$ are each independently hydrogen and X=$NH_2$.

In another embodiment of the present invention, the allantoin derivative is uric acid, or an analogue or derivative thereof having the following chemical structure, allowing for all stereoisomers thereof in pure, mixed or racemic form:

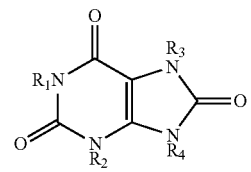

wherein:

$R_1$, $R_2$, $R_3$ and $R_4$ are each independently H, alkyl, alkenyl, alkynyl, acyl or aryl. In a certain embodiment, $R_1$, $R_2$, $R_3$ and $R_4$ are each independently hydrogen.

In another embodiment of the present invention, the comfrey-derived compound is choline, or a derivative thereof having the following chemical structure:

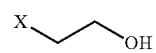

wherein X=$NH_2$, NHMe, $NMe_2$ or $NMe_3$. In a certain embodiment, the choline derivative is a pharmaceutically acceptable salt thereof including, but not limited to, inorganic acids (such as hydrochloric, sulfuric and phosphoric) and organic acids) such as acetic, propionic, butyric and tartaric). In one embodiment, the choline derivative is an inorganic salt wherein X=$NMe_3$.

In another embodiment of the present invention, the comfrey-derived compound is rosemarinic acid, or a derivative thereof having the structure of formula (4), allowing for all stereoisomers thereof in pure, mixed or racemic form:

(4)

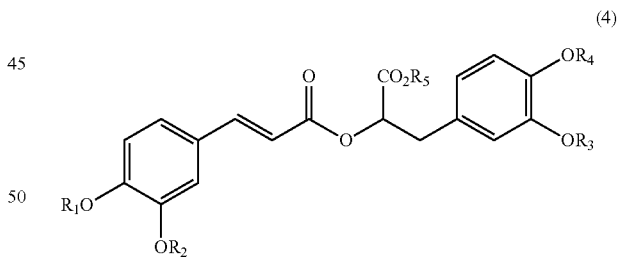

wherein $R_1$, $R_2$, $R_3$, $R_4$ and $R_5$ are each independently H, alkyl, alkenyl, alkynyl, acyl or aryl. In a certain embodiment, $R_1$, $R_2$, $R_3$, $R_4$ and $R_5$ are each independently hydrogen.

Rosemarinic acid is an ester of caffeic acid and a hydrated caffeic acid analogue, as illustrated below (the R stereoisomer is also known as salvianic acid). Thus, analogues and derivatives of a comfrey-derived product may also include comfrey metabolites (i.e., precursors) and/or in situ enzymatic hydrolysis products from rosemarinic acid post-topical administration, including, but not limited to alkylated, acylated, and otherwise derivatized rosemarinic acid analogues.

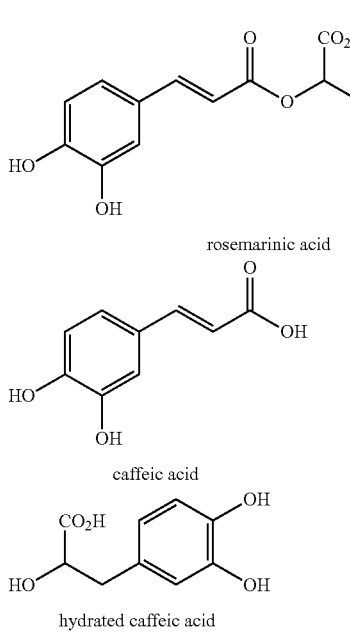

rosemarinic acid caffeic acid hydrated caffeic acid

Thus, in another embodiment of the present invention, the comfrey-derived compound is caffeic acid, or a derivative thereof having the structure of formula (5), allowing for all stereoisomers thereof in pure, mixed or racemic form:

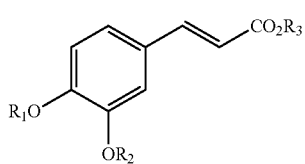

(5)

wherein $R_1$, $R_2$ and $R_3$ are each independently H, alkyl, alkenyl, alkynyl, acyl or aryl. In a certain embodiment, $R_1$, $R_2$ and $R_3$ are each independently hydrogen.

In yet another embodiment of the present invention, the comfrey-derived compound is a hydrated caffeic acid, or a derivative thereof having the structure of formula (6), allowing for all stereoisomers thereof in pure, mixed or racemic form:

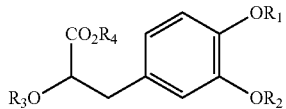

(6)

wherein $R_1$, $R_2$, $R_3$ and $R_4$ are each independently H, alkyl, alkenyl, alkynyl, acyl or aryl. In a certain embodiment, $R_1$, $R_2$, $R_3$ and $R_4$ are each independently hydrogen.

Typically, as used herein, the term "alkyl" denotes any saturated, straight chain, branched or cyclic hydrocarbon residues having from 1 to 18 carbons, the term "alkenyl" denotes any straight chain, branched or cyclic hydrocarbon residues having from 1 to 18 carbons, and incorporating at least one carbon to carbon double bond, the term "alkynyl" denotes any straight chain, branched or cyclic hydrocarbon residues having from 1 to 18 carbons, and incorporating at least one carbon to carbon triple bond and the term "acyl" denotes a residue containing the moiety C=O and not being a carboxylic acid, ester or amide. In one embodiment, the acyl residues include R-C=O, where R is H, alkyl, alkenyl, alkynyl or aryl. The term "aryl" denotes an aromatic hydrocarbon residue including, but not limited to, phenyl.

As used herein, the terms "analogue" and "derivative" are used interchangeably to denote a compound that has a chemical structure that is substantially similar to the structure of the naturally occurring compound, whilst retaining at least some of the biological function of its naturally-occurring counterpart. Analogues or derivatives may be naturally occurring or they may be constructed using synthetic techniques available to one skilled in the art.

The term "substantially similar", as used herein, typically denotes a substitution or addition of any one or more chemical substituents of the chemical structure such that the resulting analogue or derivative has at least some of the biological activity of the naturally occurring compound.

In certain embodiments, formulations that include an at least partially purified extract of comfrey or comfrey-derived compound, or an analogue or derivative thereof, are referred to herein as "non-drug" formulations. Non-drug formulations may include additional extracts, including, but not limited to, liquorice extract (e.g., liquorice root extract), Ashwagandha extract, devil's claw extract, epimedium leaf extract and lavender extract.

In other embodiments, formulations that include a comfrey-derived compound or an analogue or derivative thereof, as herein described (whether synthetic or as an at least partially purified naturally-occurring compound), are referred to herein as "drug" formulations. Topical formulations that include a combination of crude products, extracts and comfrey-derived compounds (or other partially purified active ingredient) are also envisaged as part of the present invention.

As used herein, the term "at least partially purified" typically means a compound, or an analogue or derivative thereof, which has been partially purified from its natural state. In one embodiment, the at least partially purified compound is substantially free of proteins, nucleic acids, lipids, carbohydrates or other materials with which it is naturally associated. For instance, a comfrey-derived compound, or an analogue or derivative thereof, is considered to be at least partially purified, in that it is removed from a natural source in which it is found. Optionally, a comfrey-derived compound, or an analogue or derivative thereof, can be further purified using routine and well-known methods, such as those described herein. In a certain embodiment of the present invention, the at least partially purified comfrey-derived compound, or an analogue or derivative thereof, can constitute at least about one or a few percent by weight of the total weight of the formulation, for example, at least about five percent by weight of the total weight of the formulation. In one embodiment, the at least partially purified comfrey-derived compound, or an analogue or derivative thereof, constitutes at least about twenty percent by weight of the total weight of the formulation. In another embodiment, the at least partially purified comfrey-derived compound, or an analogue or derivative thereof, can be further purified to constitute at least about fifty percent by weight of the total weight of the formulation. In a further embodiment, the at least partially purified comfrey-derived compound, or an analogue or derivative thereof, can be further purified to constitute at least about eighty percent by weight of the total weight of the formulation. In other embodiments, the at least partially purified comfrey-derived compound, or an analogue or derivative thereof, can be further purified to constitute at least about ninety percent or at least about ninety-five percent or more by weight of the total weight of the formulation. The term "substantially free", as used herein, typically refers to a preparation of a comfrey-derived compound, or an analogue or derivative thereof, having less than about 90%, 70%, 50%, 30%, 20%, 10% or 5% (by dry weight) of a molecule with which it is naturally associated.

Whilst the amount of comfrey or comfrey-derived compound, or an analogue or derivative thereof, (as herein described) in the topical formulation of the present invention may be altered by a skilled person to suit a particular use, in one embodiment, the amount of comfrey or comfrey-derived compound, or an analogue or derivative thereof, is at least 0.5% w/w of the total weight of the topical formulation. Such formulations have been found by the applicants to have particular beneficial properties in alleviating pain and discomfort associated with inflammatory and/or degenerative conditions as herein described (e.g., arthritis). In another embodiment of the present invention, the amount of comfrey or comfrey-derived compound, or an analogue or derivative thereof, will be in the range of from about 0.5% to about 40.0% of the total weight of the topical formulation of the present invention. In one example, allantoin, or an analogue or derivative thereof, is used in an amount from about 0.5% to about 10.0% of the total weight of the topical formulation of the present invention.

The penetration enhancer used in the topical formulation of the present invention includes, but is not limited to, borage oil, eucalyptus oil (e.g., eucalyptus globulus oil, Eucalyptus tereticortis oil, Eucalyptus rostrata), tetrahydropiperine (THP), alcohols (e.g., methanol, ethanol, propanol, octanol, benzyl alcohol, and the like), fatty alcohols (e.g., myristyl alcohol, cetyl alcohol, stearyl alcohol), fatty acids (e.g., oleic acid), fatty acid esters (e.g., isopropyl myristate, isopropyl palmitate), polyols (e.g., propylene glycol, polyethylene glycol, glycerol), polyethylene glycol monolaurate, lecithin, Spans™, poloxamers, Miglyol™), or combinations thereof. Other suitable penetration enhancers include, but are not limited to, diethylene glycol, monoethyl ether (available commercially as Transcutol™), n-decyl methyl sulfoxide, dimethyl sulfoxide, dimethylacetamide, laurocapram (Azone™) dimethylformamide, sucrose monooleate, amides and other nitrogenous compounds (e.g., urea, 2-pyrrolidone, 1-methyl-2-pyrrolidone, ethanolamine, diethanolamine and triethanolamine), terpenes, alkanones, organic acids (e.g., citric acid and succinic acid) and N-methyl-2-pyrrolidine (Pharmasolve™), or combinations thereof.

The amount of penetration enhancer(s) in the topical formulation according to the present invention may vary depending on the physical and chemical properties of the active agent(s) contemplated for the topical formulation (e.g., comfrey, comfrey-derived compound, tannic acid, or analogues or derivatives thereof), as well as on the chemical and physical properties of any other ingredients of the compositions. Whilst the amount of penetration enhancer used in the topical formulation of the present invention can be altered by a skilled person to suit a particular use, the penetration enhancer may be present in the topical formulations of the present invention in an amount of at least 0.05% w/w of the total weight of the topical formulation. In a certain embodiment of the present invention, the amount of penetration enhancer will be in the range of from about 0.05% to about 75% of the total weight of the topical formulation of the present invention.

The ratio between the amount(s) of active agent(s) and of penetration enhancer(s) in the topical formulation according to the present invention may also vary considerably depending on the physical and chemical properties of the active agent(s) therein, its pharmacological activity and the treated condition and the therapy which is desired, as well as on the properties of any other ingredients in the topical formulation. In one embodiment, the topical formulation includes an amount of active agent(s) and an amount of penetration enhancer(s) that is from about 1:1 to about 1:4. In another embodiment, the topical formulation includes an amount of active agent(s) and an amount of penetration enhancer(s) that is from about 1:1 to about 1:2.

In another embodiment of the present invention, the amount of penetration enhancer used in the topical formulation is about 0.2% to about 1.0% of the total weight of the topical formulation.

In addition to a penetration enhancer and comfrey or a comfrey-derived compound, or an analogue or derivative thereof, the topical formulation of the present invention may further include tannic acid, or an analogue or derivative thereof. In one embodiment, the tannic acid, or analogue or derivative thereof, is an at least partially purified compound (as hereinbefore described). The tannic acid (or analogue or derivative thereof) may be prepared as an at least partially purified compound during (e.g., at the same time as) preparation of the comfrey or comfrey-derived compound (or analogue or derivative thereof) or it may be prepared in isolation as an at least partially purified compound and subsequently combined with comfrey or the comfrey-derived compound (or analogue or derivative thereof), or a combination thereof. In a certain embodiment of the present invention, tannic acid is prepared as an at least partially purified compound and subsequently combined with comfrey or a comfrey-derived compound (or analogue or derivative thereof).

Tannic acid is a polymer of gallic acid molecules and glucose. The structure for tannic acid is shown below as a polyphenolic derivatized sugar:

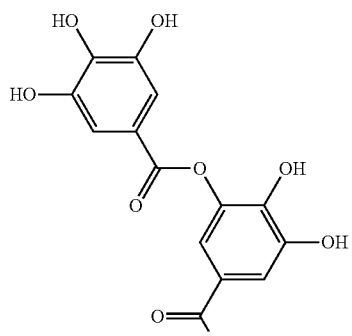
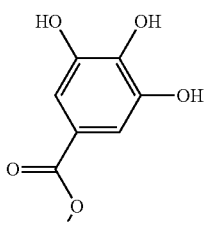
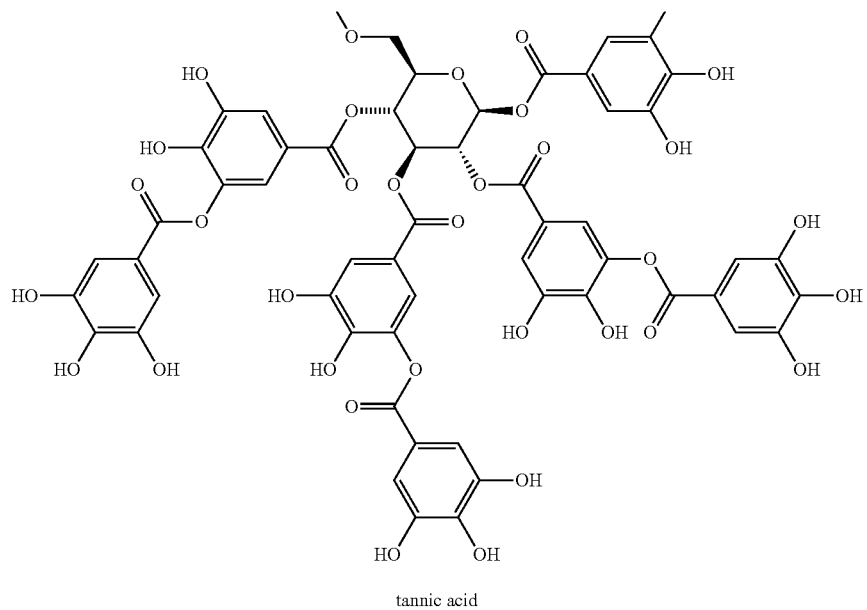

tannic acid

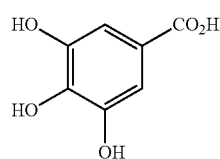

gallic acid

Reduced to its component parts, tannic acid is constructed of multiple gallic acid residues esterified to a simple hexose sugar (i.e., glucose).

Thus, in an embodiment of the present invention, the tannic acid derivative is gallic acid, or an ester thereof (including, but not limited to, a gallic acid dimer), either singularly or in combination and/or partially assembled towards tannic acid. In yet another embodiment, the tannic acid analogue or derivative may be an alkylated, acylated or otherwise derivatized tannic at the phenolic positions. In yet another embodiment, the tannic acid analogue or derivative may act as pro-drug releasing tannic acid in situ through the action of enzymes post administration.

Tannic acid analogues also include, but are not limited to, rosemarinic acid, caffeic acid, curcumin, resveratrol, salvianolic acid B (the oxidative dimer of rosemarinic acid) and ferulic acid (a simple phenolic which bears structural similarity to curcumin).

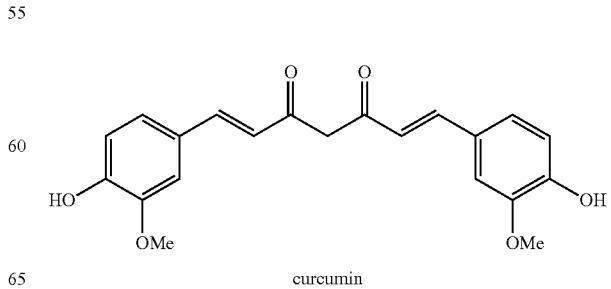

curcumin

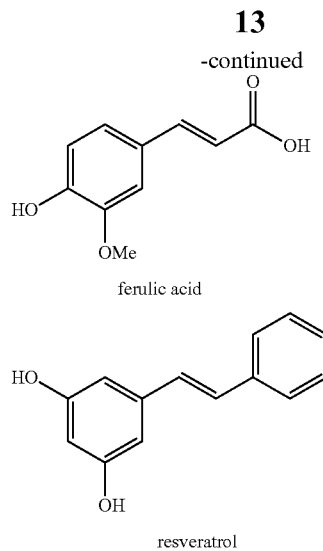

ferulic acid resveratrol

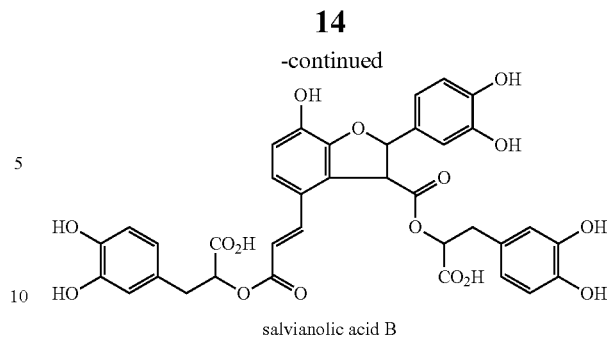

salvianolic acid B

Also envisaged are tannic analogues or derivatives as herein described that have undergone oxidative dimerization with differing regiochemistry, ring sizes and stereochemistry.

Thus, in one embodiment of the present invention, the tannic acid analogue or derivative has the structure of formula (7), allowing for all stereoisomers thereof in pure, mixed or racemic form:

(7)

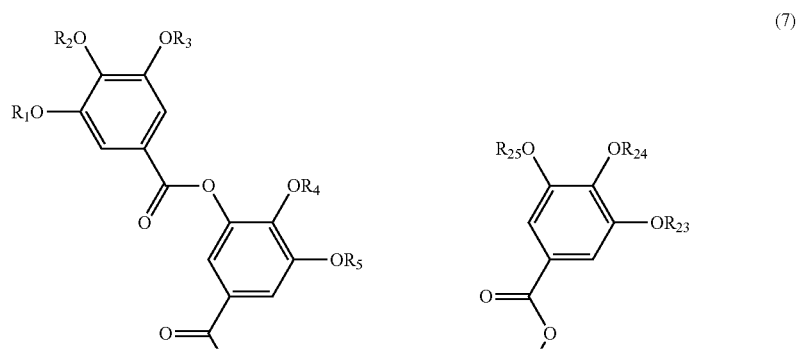

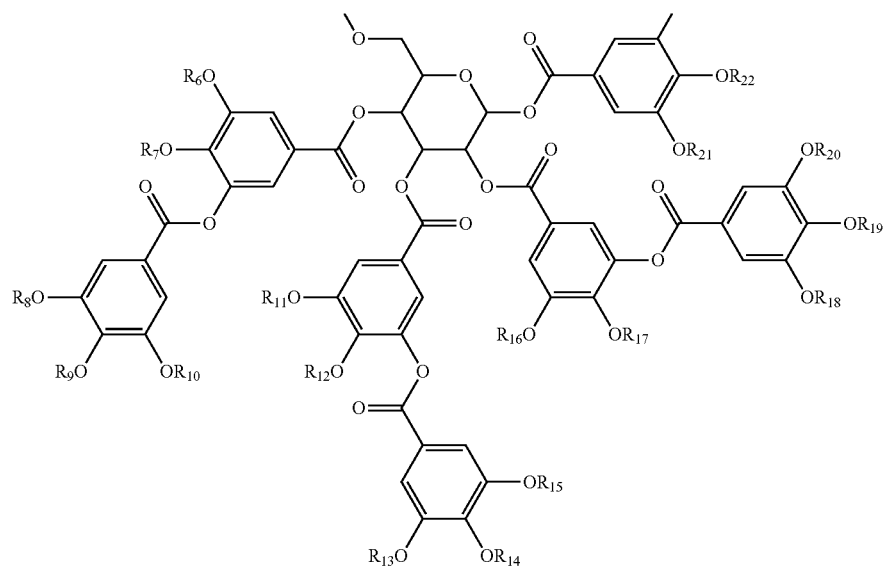

wherein $R_1$, $R_2$, $R_3$, $R_a$, $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$ and $R_{25}$ are each independently H, alkyl, alkenyl, alkynyl, acyl or aryl. In a certain embodiment, $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$ and $R_{25}$ are each independently hydrogen.

In yet another embodiment of the present invention, the tannic acid analogue or derivative is gallic acid or an analogue or derivative thereof having the structure of formula (8), allowing for all stereoisomers thereof in pure, mixed or racemic form:

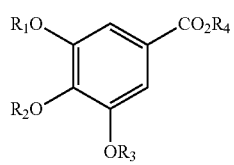

(8)

wherein $R_1$, $R_2$, $R_3$ and $R_4$ are each independently H, alkyl, alkenyl, alkynyl, acyl or aryl. In a certain embodiment, $R_1$, $R_2$, $R_3$ and $R_4$ are each independently hydrogen.

In yet another embodiment of the present invention, the tannic acid analogue or derivative is curcumin or an analogue or derivative thereof having the structure of formula (9), allowing for all stereoisomers thereof in pure, mixed or racemic form:

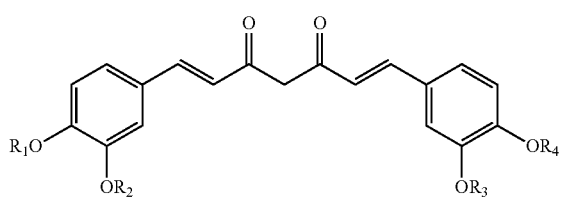

(9)

wherein $R_1$, $R_2$, $R_3$ and $R_4$ are each independently H, alkyl, alkenyl, alkynyl, acyl or aryl. In a certain embodiment, $R_1$ and $R_4$ are each independently hydrogen and $R_2$ and $R_3$ are each independently methyl (Me).

In yet another embodiment of the present invention, the tannic acid analogue or derivative is ferulic acid or an analogue or derivative thereof having the structure of formula (10), allowing for all stereoisomers thereof in pure, mixed or racemic form:

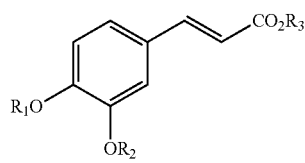

(10)

wherein $R_1$, $R_2$ and $R_3$ are each independently H, alkyl, alkenyl, alkynyl, acyl or aryl. In a certain embodiment, $R_1$ and $R_3$ are each independently hydrogen and $R_2$ is methyl (Me).

In yet another embodiment of the present invention, the tannic acid analogue or derivative is resveratrol or an analogue or derivative thereof having the structure of formula (11), allowing for all stereoisomers thereof in pure, mixed or racemic form:

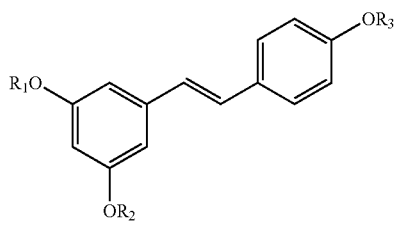

(11)

wherein $R_1$, $R_2$ and $R_3$ are each independently H, alkyl, alkenyl, alkynyl, acyl or aryl. In a certain embodiment, $R_1$, $R_2$ and $R_3$ are each independently hydrogen.

For the purposes of the present invention, tannic acid, or an analogue or derivative thereof, may be used in the form of a technical grade, an at least partially purified extract (as hereinbefore described), such as from nutgall, a standardized extract or, alternatively, it may be of a substantially pure, pharmaceutical grade, or a derivative thereof. In one embodiment, tannic acid is selected from the group consisting of (i) an extract of *Caesalpinia spinosa*, (ii) a mixture of an extracts from *Caesalpinia spinosa, Quecus infectoria* and *Rhus semialata*, (iii) an extract from the galls of *Quecus infectoria* (iv) an extract from the galls of *Rhus semialata*, (v) an extract from the wood of *Schinopsis lorentzii*, and (vi) an extract from the wood of *Castanea sativa* (chestnut), Whilst the amount of tannic acid (or an analogue or derivative thereof) used in the topical formulation of the present invention can be altered by a skilled person to suit a particular use, it may be present in an amount that is at least 2% of the total weight of the topical formulation. In one embodiment, the tannic acid (or an analogue or derivative thereof) may be used in an amount that is from about 2% to about 20% of the total weight of the topical formulation.

In yet another aspect of the present invention, there is provided a topical formulation including (i) comfrey or a comfrey-derived compound, or an analogue or derivative thereof, and (ii) tannic acid, or an analogue or derivative thereof, as herein described. Such formulation may further include a penetration enhancer, as herein described.

The tannic acid (or analogue or derivative thereof) may be prepared as an at least partially purified compound during (e.g., at the same time as) preparation of the comfrey or comfrey-derived compound (or analogue or derivative thereof) or it may be prepared in isolation as an at least partially purified compound and subsequently combined with comfrey or the comfrey-derived compound (or analogue or derivative thereof), or a combination thereof. In a certain embodiment of the present invention, tannic acid is prepared as an at least partially purified compound and subsequently combined with comfrey or a comfrey-derived compound (or analogue or derivative thereof).

In yet another embodiment of the present invention, the comfrey-derived compound analogues or derivatives and the tannic acid analogues or derivatives are pharmaceutically acceptable salts or prodrugs thereof.

As used herein, the phrase "pharmaceutically acceptable prodrug" typically denotes a compound that may be converted under physiological conditions or by solvolysis to the specified compound (e.g. active agent) or to a pharmaceutically acceptable salt thereof.

As used herein, the phrase "pharmaceutically acceptable salt" typically denotes a salt that retains the biological effectiveness of the free acids and bases of the specified compound and that is not biologically or otherwise undesirable. A compound for use in the formulations of the present invention may possess a sufficiently acidic, a sufficiently basic, or both functional groups, and accordingly react with any of a number of inorganic or organic bases, and inorganic and organic acids, to form a pharmaceutically acceptable salt. Exemplary pharmaceutically acceptable salts include those salts prepared by reaction of the compounds of the present invention with a mineral or organic acid or an inorganic base, including, but not limited to, sulfates, pyrosulfates, bisulfates, sulfites, bisulfites, phosphates, monohydrophosphates, dihydrophosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4 dioates, hexyne-1,6-dioates, benzoates, chlorobenzoates, methyl benzoates, dinitrobenzoates, hydroxybenzoates, methoxybenzoates, phthalates, sulfonates, xylenesulfonates, phenylacetates, phenylpropionates, phenylbutyrates, citrates, lactates, gamma-hydroxybutyrates, glycollates, tartrates, methanesulfonates, propanesulfonates, naphthalene-1-sulfonates, naphthalene-2-sulfonates, and mandelates.

Depending on the type and amount of ingredients therein (e.g., penetration enhancer, comfrey, comfrey-derived compound, tannic acid, or analogues or derivatives thereof), the desired consistency and the contemplated mode of application of the topical formulation of the present invention, the carrier material in the topical formulation according to the present composition may include carrier materials such as pharmacologically-acceptable oils and water and/or such supplementary pharmaceutical adjuvants which are conventionally used in topical formulations (e.g., in conventional bases for ointments, creams, and gels). In many cases it may be advisable to incorporate a structure-forming, thickening or gel-forming agent into the composition. Suitable agents are, in particular, highly dispersed silicic acid (e.g., the commercial product "Aerosil"), bentonites, modified montmorillonites such as alkyl ammonium salts of montmorillonites (e.g., the commercial product "Bentone"), wherein the alkylgroups may contain 1 to 20 carbon atoms (e.g., dimethyl-dialkyl-ammonium salts wherein the alkylgroups contain 16 to 18 carbon atoms), organic structure-forming, thickening and suspending agents (e.g., Xantham gum, Carrageenan gum, cetostearylic alcohol) and modified castor oil products (e.g., the commercial product "Antisettle CVP"™)

Pharmaceutical adjuvants which may be used in the topical formulation of the present invention includes adjuvants which are conventionally applied in the preparation of ointments, jellies, and lotions, for example thickening agents, emulsifying agents, antioxidents: hygroscopic agents, anti-molding agents, perfumes, and the like.

The topical formulations according to the present invention may be prepared in any conventional manner. In one embodiment, tannic acid (or an analogue or derivative thereof), glycerin, methyl paraben and extracts other than comfrey are mixed in a side vessel and agitated until the solution is complete. In another side vessel, castor oil is blended with any essential oils until homogeneous. In an appropriate batch kettle, aloe vera liquid is added to sodium hydroxymethylglycinate and the gelling agent with good agitation. The tannic acid/glycerin mixture is then added to the batch kettle with good agitation, followed by the castor oil mixture, again with good agitation. The combined solution is then agitated until smooth.

The topical formulation according to the present invention may be aqueous (i.e., containing water), or it may be nonaqueous and optionally used in combination with an occlusive overlayer so that moisture evaporating from the body surface is maintained within the formulation upon application to the body surface and thereafter.

It has been found that a formulation that includes a penetration enhancer and a comfrey-derived compound (or an analogue or derivative thereof) or a formulation that includes a comfrey-derived compound (or an analogue or derivative thereof) and tannic acid (or an analogue or derivative thereof) can provide long term relief to ailments, such as osteoarthritis. Without being bound by theory, it is believed that the active components in the formulations of the present invention are able to act synergistically upon a site of inflammation and/or degeneration and provide long lasting, if not permanent, relief after a course of treatment. In one embodiment, a suitable course of treatment is 1 to 5 applications per day over a period of about 1 to about 100 days. In another embodiment, a suitable course of treatment is 1 to 5 applications per day over a period of about 1 to about 180 days. In another embodiment, a suitable course of treatment is 3 to 4 applications per day over a period of about 15 to about 90 days.

Further, with the presence of a penetration enhancer, the formulation can be applied directly without the need for a bandage or pressure pad to be applied, as occurs now with some comfrey-based formulations.

The topical formulations according to the present invention may take the form of compositions suitable for topical application to the body surface, and may comprise, for example, a cream, lotion, solution (e.g., liquid spray), gel, ointment, paste, plaster, paint, bioadhesive, or the like. A typical gel formulation may comprise glycerin (5-20% w/w), castor oil (10-25% w/w), tannic acid (2-20% w/w), ashwagandha extract (0.5-2.0% w/w), kelp extract (0.5-2.0% w/w), total comfrey extract (0.5-40% w/w), aloe vera liquid (40-60% w/w), lavender oil (0.1-0.3% w/w), eucalyptus oil (0.1-5% w/w), methyl paraben (0.1-0.3% w/w) and sodium hydroxymethylglycinate (0.1-0.3% w/w).

Ointments

Ointments, as is well known in the art, are semisolid preparations that are typically based on petrolatum or other petroleum derivatives. The specific ointment base to be used, as will be appreciated by those skilled in the art, is one that will provide for optimum delivery of the active agent(s), and which may also provide for other desired characteristics as well (e.g., emolliency or the like). As with other carriers or vehicles, an ointment base is typically inert, stable, nonirritating and nonsensitizing. Ointment bases may be grouped in four classes: oleaginous bases; emulsifiable bases; emulsion bases; and water-soluble bases. Oleaginous ointment bases include, for example, vegetable oils, fats obtained from animals, and semisolid hydrocarbons obtained from petroleum. Emulsifiable ointment bases, also known as absorbent ointment bases, contain little or no water and include, for example, hydroxystearin sulfate, anhydrous lanolin and hydrophilic petrolatum. Emulsion ointment bases are either water-in-oil (w/o) emulsions or oil-in-water (o/w) emulsions, and include, for example, cetyl alcohol, glyceryl monostearate, lanolin, stearic acid and polyethylene glycols of varying molecular weight, or combinations thereof. Other examples of suitable hydrocarbon bases include, but are not limited to, hard, soft, or liquid paraffin, glycerol, beeswax, a metallic soap, a mucilage, an oil of natural origin (such as almond, corn, arachis, castor or olive oil), wool fat or its derivative, a fatty acid (such as stearic acid or oleic acid), or combinations thereof.

Creams

Creams, as also well known in the art, are viscous liquid or semisolid oil-in-water emulsions. Cream bases can be water-washable, and contain an oil phase, an emulsifier, and an aqueous phase. The oil phase, also called the "internal" phase, may include petrolatum and a fatty alcohol such as cetyl or stearyl alcohol. The aqueous phase usually, although not necessarily, exceeds the oil phase in volume, and generally contains a humectant. The emulsifier in a cream formulation is generally a nonionic, anionic, cationic, or amphoteric surfactant, or combinations thereof.

Gels

As will be appreciated those persons skilled in the art, gel formulations are typically semisolid, suspension-type systems. Single-phase gels typically contain organic macromolecules distributed substantially uniformly throughout the carrier liquid, which is typically aqueous, but may also contain an alcohol and, optionally, an oil. Exemplary "organic macromolecules" (i.e., gelling agents), are cross-linked acrylic acid polymers such as the "carbomer" family of polymers (e.g., carboxypolyalkylenes that may be obtained commercially under the Carbopol™). Also exemplified are hydrophilic polymers such as polyethylene oxides, polyoxyethylene-polyoxypropylene copolymers, polyvinylalcohol and polyvinyl pyrrolidones; cellulosic polymers such as hydroxypropyl cellulose, hydroxyethyl cellulose, hydroxypropyl methylcellulose, carboxymethyl cellulose, hydroxypropyl methylcellulose phthalate, and methyl cellulose; gums such as carrageenan gum, tragacanth and xanthan gum; sodium alginate; and gelatin. Other examples of suitable gel forming agents include carboxy-poly-methylene derivatives such as carbopol and pectins. In one embodiment of the present invention, the gelling agent is Xantham gum and/or carrageenan gum.

In one embodiment, the thickening or gelling agents may be present in the composition generally in a w/w % amount of from about 0.2% to 5.0%. In another embodiment, the thickening or gelling agents may be present in the composition generally in a w/w % amount of from about 0.1% to 1.0%. In yet another embodiment of the present invention, the topical gel formulation may include a gelling agent in an amount of up to 3.0% w/w (e.g., Xantham gum).

In order to prepare a uniform gel, a diluent such as alcohol can be added, or the gelling agent can be dispersed by trituration, mechanical mixing or stirring, or combinations thereof.

Lotions

Lotions are typically preparations to be applied to the skin surface without friction, and are typically liquid or semiliquid preparations in which solid particles, including the active agent (e.g., comfrey, tannic acid), are present in a water or alcohol base. Lotions are usually suspensions of solids, and may, for the present purpose, comprise a liquid oily emulsion of the oil-in-water type. Lotions can be used to treat large body areas because of the ease of applying a more fluid composition. It is generally desirable that the insoluble matter in a lotion be finely divided. Thus, lotions will typically contain suspending agents to produce better dispersions, as well as compounds useful for localizing and holding the active agent in contact with the skin (e.g., methylcellulose), sodium carboxymethyl-cellulose, or the like. Lotions may also include an agent to hasten drying and cooling of the solution on the skin, such as alcohol or acetone. They may further include a moisturizer, such as glycerol, or an oil, such as castor oil or arachis oil.

Topical formulations of the present invention may also be prepared with liposomes, and/or micelles.

Liposomes are microscopic vesicles having a lipid wall comprising a lipid bilayer, and can be used as delivery systems herein. Generally, liposome formulations are employed for poorly soluble or insoluble agents. Liposomal preparations for use in the instant invention include cationic (positively charged), anionic (negatively charged) and neutral preparations. Cationic liposomes are readily available. For example, N[1-2,3-dioleyloxy)propyl]-N,N,N-triethylammonium (DOTMA) liposomes are available under the tradename Lipofectin™. Similarly, anionic and neutral liposomes are readily available as well (e.g., Avanti Polar Lipids, Birmingham, Alabama), or can be easily prepared using readily available materials. Such materials include phosphatidyl choline, cholesterol, phosphatidyl ethanolamine, dioleoylphosphatidyl choline (DOPC), dioleoylphosphatidyl glycerol (DOPG), dioleoylphoshatidyl ethanolamine (DOPE), among others. These materials can also be mixed with DOTMA in appropriate ratios. Methods for making liposomes using these materials are well known in the art.

Micelles, in an aqueous solution, are known in the art to be comprised of surfactant molecules arranged so that their polar headgroups form an outer spherical shell, while the hydrophobic, hydrocarbon chains are oriented towards the center of the sphere, forming a core. Micelles form in an aqueous solution containing a surfactant at a high enough concentration so that micelles naturally result. Surfactants useful for forming micelles include, but are not limited to, potassium laurate, sodium octane sulfonate, sodium decane sulfonate, sodium dodecane sulfonate, sodium lauryl sulfate, docusate sodium, decyltrimethylammonium bromide, dodecyltrimethylammonium bromide, tetradecyltrimethylammonium bromide, tetradecyltrimethylammonium chloride, dodecylammonium chloride, polyoxyl 8 dodecyl ether, polyoxyl 12 dodecyl ether, nonoxynol 10 and nonoxynol 30.

Micelle formulations can be used in conjunction with the present invention either by incorporation into the reservoir of a topical delivery system, or into a topical formulation to be applied to the body surface.

Various additives, known to those skilled in the art, may also be included in the topical formulations of the present invention. For example, solvents, including relatively small amounts of alcohol, may be used to solubilize certain formulation components. Suitable solvents include glycerin, SD 40 alcohol, lecithin, poloxamers, Miglyol™ and methyl pyrrolidone, or combinations thereof. Other suitable solvents include glycerol, diluted alcohol isopropanol, hexylene glycol and propylene glycol.

Menthol may be also be added to the topical formulation of the present invention.

In one embodiment, surfactant(s) may be employed in the topical formulation according to the present invention, for example, in an amount of from about 0.5% to about 5.0% w/w. Suitable surfactants may include, but are not limited to, sodium lauryl sulfate, benzalkonium chloride, cetylpyridinium chloride, sodium laurate, cetyltrimethylammonium bromide, Poloxamer (231, 182, 184), Tween (20, 40, 60, 80) and Span™.

Other agents may also be added to the topical formulation of the present invention include antimicrobial agents, to prevent spoilage upon storage (i.e., to inhibit growth of microbes such as yeasts and molds. Suitable antimicrobial agents are typically selected from the group consisting of the methyl and propyl esters of p-hydroxybenzoic acid (i.e., methyl and propyl paraben), sodium benzoate, sodium hydroxymethylglycinate, sorbic acid, imidurea, potassium iodide and combinations thereof.

The formulations may also contain irritation-mitigating additives to minimize or eliminate the possibility of skin irritation or skin damage resulting from the pharmacologically active base or other components of the composition. Suitable irritation-mitigating additives include, for example: $\alpha$-tocopherol; monoamine oxidase inhibitors, particularly phenyl alcohols such as 2-phenyl-1-ethanol; glycerin; ascorbic acids and ascorbates; ionophores such as monensin; amphiphilic amines; ammonium chloride; N-acetylcysteine; cis-urocanic acid; capsaicin; and chloroquine. The irritant-mitigating additive, if present, may be incorporated into the present formulations at a concentration effective to mitigate irritation or skin damage, typically representing from about 0.05% to about 1.0% (w/w).

The topical formulation of the present invention may also be administered through the skin or mucosal tissue using a conventional skin patch, wherein the active agent(s) (e.g., comfrey, comfrey-derived compound, penetration enhancer, tannic acid, etc) is/are contained within a laminated structure that serves as a delivery device to be affixed to the body surface. In such a structure, the topical formulation is contained in a layer, or "reservoir," underlying an upper backing layer. The laminated structure may contain a single reservoir, or it may contain multiple reservoirs.

In one embodiment, the reservoir comprises a polymeric matrix of a pharmaceutically acceptable adhesive material that serves to affix the system to the skin during delivery of the topical formulation. Typically, the adhesive material is a pressure-sensitive adhesive (PSA) that is suitable for long-term skin contact, and that should be physically and chemically compatible with the topical formulation. Examples of suitable adhesive materials include, but are not limited to, the following: polyethylenes; polysiloxanes; polyisobutylenes; polyacrylates; polyacrylamides; polyurethanes; plasticized ethylene-vinyl acetate copolymers; and tacky rubbers such as polyisobutene, polybutadiene, polystyrene-isoprene copolymers, polystyrene-butadiene copolymers, and neoprene (polychloroprene). Preferred adhesives are polyisobutylenes.

The backing layer functions as the primary structural element of the transdermal system and provides the device with flexibility and, preferably, occlusivity. The material used for the backing layer should be inert and incapable of absorbing any one or more of the active agents included in the topical formulation contained within the device. The backing is preferably comprised of a flexible elastomeric material that serves as a protective covering to prevent loss of drug and/or vehicle via transmission through the upper surface of the patch, and will preferably impart a degree of occlusivity to the system, such that the area of the body surface covered by the patch becomes hydrated during use. The material used for the backing layer should permit the device to follow the contours of the skin and be worn comfortably on areas of skin such as at joints or other points of flexure, that are normally subjected to mechanical strain, with little or no likelihood of the device disengaging from the skin due to differences in the flexibility or resiliency of the skin and the device. The materials used as the backing layer are either occlusive or permeable, as noted above, although occlusive backings are preferred, and are generally derived from synthetic polymers (e.g., polyester, polyethylene, polypropylene, polyurethane, polyvinylidine chloride, and polyether amide), natural polymers (e.g., cellulosic materials), or macroporous woven and nonwoven materials.

During storage and prior to use, the laminated structure may include a release liner. Immediately prior to use, this layer can be removed from the device so that the device may be affixed to the skin. The release liner is typically made from an impermeable material, and is a disposable element that serves only to protect the device prior to application. Typically, the release liner is formed from a material impermeable to one or more components of the topical formulation contained in the device, and which can be easily stripped from the patch prior to use.

In an alternative embodiment, the topical formulation-containing reservoir and skin contact adhesive are present as separate and distinct layers, with the adhesive underlying the reservoir. In such a case, the reservoir may be a polymeric matrix as described above. Alternatively, the reservoir may be comprised of a liquid or semisolid topical formulation contained in a closed compartment or "pouch," or it may be a hydrogel reservoir, or may take some other form. As will be appreciated by those skilled in the art, hydrogels are macromolecular networks that absorb water and thus swell but do not dissolve in water. That is, hydrogels contain hydrophilic functional groups that provide for water absorption, but the hydrogels are comprised of crosslinked polymers that give rise to aqueous insolubility. Generally, then, hydrogels are comprised of crosslinked hydrophilic polymers such as a polyurethane, a polyvinyl alcohol, a polyacrylic acid, a polyoxyethylene, a polyvinylpyrrolidone, a poly(hydroxyethyl methacrylate) (poly(HEMA)), or a copolymer or mixture thereof. Particularly preferred hydrophilic polymers are copolymers of HEMA and polyvinylpyrrolidone.

Additional layers (e.g., intermediate fabric layers and/or rate-controlling membranes), may also be present in any of these delivery systems. Fabric layers may be used to facilitate fabrication of the device, while a rate-controlling membrane may be used to control the rate at which the topical formulation permeates out of the device. A rate-controlling membrane, if present, will be included in the system on the skin side of one or more of the reservoirs. The materials used to form such a membrane are typically selected to limit the flux of one or more components contained in the topical formulation. Representative materials useful for forming rate-controlling membranes include polyolefins such as polyethylene and polypropylene, polyamides, polyesters, ethylene-ethacrylate copolymer, ethylene-vinyl acetate copolymer, ethylene-vinyl methylacetate copolymer, ethylene-vinyl ethylacetate copolymer, ethylene-vinyl propylacetate copolymer, polyisoprene, polyacrylonitrile, ethylene-propylene copolymer, and the like.

Generally, the underlying surface of the transdermal device (i.e., the skin contact area) has an area in the range of about 0.25 cm² to 200 cm², preferably 1 cm² to 25 cm², more preferably 2 cm² to 10 cm². That area will vary, of course, with the size of the area to be treated.

Such delivery systems may be fabricated using conventional coating and laminating techniques known in the art. For example, adhesive matrix systems can be prepared by casting a fluid admixture of an adhesive and the topical formulation of the present invention onto the backing layer, followed by lamination of the release liner. Similarly, the adhesive mixture may be cast onto the release liner, followed by lamination of the backing layer. Alternatively, the reservoir may be prepared in the absence of topical formulation, and then loaded by "soaking" in the topical formulation. In general, these patches are fabricated by solvent evaporation, film casting, melt extrusion, thin film lamination, die cutting, or the like. The topical formulation will generally be incorporated into the device during patch manufacture rather than subsequent to preparation of the device.

The delivery system may also include an adhesive overlayer that also serves as a backing for the delivery system is used to better secure the patch to the body surface. This overlayer is sized such that it extends beyond the reservoir so that adhesive on the overlayer comes into contact with the body surface. The overlayer is useful because the adhesive/reservoir layer may lose its adhesion a few hours after application due to hydration. By incorporating such adhesive overlayer, the delivery system remains in place for the required period of time.

In another embodiment of the present invention, the delivery system includes nanoparticles. The nanoparticles may be dispersed within a microemulsion in the formulation of the present invention, or as part of the vehicle of such formulations, for use in delivery of the active agent(s) through the skin. Without being bound by theory, such nanoparticles will readily penetrate the skin and may be retained within specific layers of the skin. In one embodiment, the nanoparticles have a core comprised of an iron ore that is strongly attracted by a magnet. In one embodiment, the nanoparticles include magnetite, which in one embodiment refers to a molecule with a general formula of $Fe_3O_4$. The nanoparticles may include chemical equivalents of magnetite, such as, for example, and in one embodiment, $(Fe,M)OFe_2O_3$ where M may be, in one embodiment, Zn, Co, Ni, Mn, Cr, Au, or Ag. In one embodiment, the nanoparticles for use in the delivery system and according to the methods of this invention range in size from 1-100 nm.

Polymers may also be conjugated to the nanoparticles by an array of means well known by those skilled in the art. The active agent(s), in turn, may be conjugated to the polymer, conjugated to the nanoparticle or, as a function of the physicochemical properties of the compound, may be directly affixed to the nanoparticle. The choice of polymer utilized may be a function of the particles employed. In one embodiment, the polymer includes polyacrylic acid, polystyrene sulfonic acid, polyvinyl sulfonic acid, polyethylene oxide, polypropylene oxide, polyvinyl alcohol, photopolymerizable macromers, biodegradable polymers such as but not limited to PLGA, or a combination thereof. In another embodiment, the polymer includes a surfactant, a polyethylene glycol, a lignosulfonate, a polyacrylamide or a biopolymer. In yet another embodiment, the biopolymer includes polypeptides, cellulose and its derivatives such as hydroxyethyl cellulose and carboxymethyl cellulose, alginate, chitosan, lipid, dextran, starch, gellan gum or other polysaccharides, or a combination thereof.

The topical formulations of the present invention may also include other compositions that facilitate the delivery of the active ingredient(s) through the skin. For example, in one embodiment of the present invention, the active agents(s) are formulated into macromolecular assemblies using nanoparticles, as described, for example, in WO 2006/113668, WO 2006/129127 and U.S. 60/671,892 as published (the entire contents of which are incorporated herein by reference). Without being bound by theory, macromolecular assemblies of this type typically mimic natural lipoprotein and are therefore said to solubilize hydrophobic active agents to facilitate their delivery (e.g. transdermal delivery) by penetrating the inter-corneocyte lipid layer of the skin and also the hydrophilic pores. Without being bound by theory, the macromolecular assemblies may become trapped within the stratum corneum of the skin and therefore act as reservoirs for the active agent(s) to enable sustained release into the deeper layers of the skin and thereby provide a distinct therapeutic profile. This could in turn enhance the efficacy of the active agent(s), reduce the number of applications required and quantity of active agent(s) required, and could therefore be more convenient for the patient.

These and other types and configurations of topically applied delivery systems may be used alone or in combination to facilitate the delivery of the active agent(s) included in the formulations of the present invention, as will be appreciated by those skilled in the art of, for example, topical drug delivery. Thus, it is to be understood that the delivery system may include any single or combinations of the embodiments listed herein.

Any suitable emollient or skin conditioning agent may optionally be included in the topical formulations of this invention. Suitable emollients include, but are not limited to, cholesterol, glycerine, glyceryl monostearate, isopropyl myristate, isopropyl palmitate, cetostearyl alcohol, lanolin alcohols and mixtures thereof. Optionally, dimethicone, mineral oil or white soft paraffin may also be incorporated into the formulations in relatively small amounts to act as a skin conditioner. The emollient or skin conditioning agent may be present in the topical formulations of this invention in a w/w % amount of from about 0.5% to about 50%. For example, in the gel formulations of this invention, the emollient or skin conditioning agent may generally be present in an amount of up to about 50% w/w. In another embodiment, the cream or lotion formulations of this invention may include the emollient or skin conditioning agent in an amount of from about 0.5% to about 15% w/w.

The formulations of the present invention may optionally include a buffer or neutralizing agent. Examples of suitable buffers include, but are not limited to, citric acid, lactic acid, oleic acid, sodium phosphate, water, triethanolamine, sodium citrate, hydrochloric acid and the like. The buffering agent may be present in the composition in any suitable buffering effective amount. The gel formulation will generally contain a base, such as for example, sodium hydroxide, triethanolamine and the like. The gel formulations of this invention will also generally include a volatile solvent, such as for example, ethanol, isopropanol and the like.

The topical formulation of the present invention may optionally include preservative or antioxidant components. Examples of such preservative and antioxidant include, but are not limited to, alkyl alcohols, benzyl alcohol, butylated hydroxyanisole, butylated hydroxytoluene (methyl and propyl paraben), butyl paraben, disodium edetate, citric acid and the like. The preservative and/or antioxidant may be present in the formulations of this invention in a w/w amount of from about 0.05 to about 5.0% w/w. In another embodiment, the preservative and/or antioxidant may be present in the formulations of this invention in an amount of from about 0.25% to about 0.5% w/w.

In certain embodiments, the topical formulation of the present invention may also include other active ingredients including, but not limited to, arginine, asparagine, an Ashwagandha extract, withanolides or alkaloids derived from Ashwagandha, brown vinegar, brewer's yeast, castor oil, ricinoleic acid, devil's claw and/or a herpagoside derived therefrom, epimedium leaf extract, icarlin, eucalyptus oil (e.g., eucalyptus globulus oil, Eucalyptus tereticortis oil, Eucalyptus rostrata), cineole or other terpenes derived from eucalyptus oil, frankincense, boswellic acid, glycerin, kelp, potassium iodate, algin, lavender, 1,8-cineole, linalol, lynalol acetate, nut gall extract, lecithin, liquorice extract (e.g., liquorice root extract), glabridin, glycyrrhizic acid, glycyrrhizic acid monoammonium salt, 10-beta-glycyrrhetinic acid, ellagic acid, turmeric, curcumin, tetrahydro curcuminoid (THC), or any combination thereof. Without being bound by theory, the other active ingredient(s) may contribute, at least in part, to the efficacy of the formulation of the present invention by acting directly or indirectly on a physiological or pathophysiological pathway.

As used herein, the terms "active ingredient", "active agent" and the like typically denote a compound that contributes, at least in part, to the efficacy of the formulation of the present invention by acting either directly or indirectly on a physiological or pathophysiological pathway. For instance, without being bound by theory, tannic acid (or an analogue or derivative thereof) may be contributing to the efficacy of the formulations of the present invention indirectly by enhancing the efficacy of any other active ingredient (e.g. comfrey or a comfrey-derived compound or an analogue or derivative thereof), rather than acting directly on a physiological or pathophysiological pathway, whether that pathway is the same or different from the pathway that is targeted by the other active ingredient.

In one embodiment of the present invention, the other active ingredient is eucalyptus oil, as herein described. The amount of eucalyptus oil in a formulation of the present invention may vary according to the intended use. For instance, in one embodiment, the eucalyptus oil is present in a homeopathic quantity as known to those skilled in the art of homeopathic formulations, either as the mother tincture (i.e., as a solution of eucalyptus globulus oil and alcohol made according to standards set by the Homeopathic Pharmacopeia of the United States) or in lower concentrations (e.g., diluted from about 1 in 10 to about 1 in 10,000).

Without being bound by theory, eucalyptus globulus oil may be used consistent with homeopathic principles for the relief of an inflammatory and/or degenerative condition including, but not limited to, arthritis. In a certain embodiment, the topical formulation of the present invention includes from about 0.1% to about 4% w/w of eucalyptus globulus oil. Eucalyptus oil may be obtained by any process known in the art, or it may be purchased from a commercial source such as Biochemica International.

In another embodiment, the other active ingredient may be a crude product (e.g., Ashwagandha), an extract thereof (e.g., a botanical extract such as Ashwagandha extract) or a naturally-occurring compound that is at least partially purified, for example, from a crude botanical extract by methods known to those skilled in the art, and optionally purified to a substantially pure form as required. In another embodiment, the other active ingredient may be synthetic, manufactured by processes known to those skilled in the art. Combinations of naturally-occurring and synthetic compounds are also envisaged in certain embodiments of the present invention.

Methods of Manufacture

In another aspect of the present invention, there is provided a method of manufacturing a topical formulation, the method including combining (i) comfrey or a comfrey-derived compound, or an analogue or derivative thereof (as herein described) with (ii) a penetration enhancer (as herein described). In one embodiment, the method includes the step of adding (iii) tannic acid, or an analogue or derivative thereof (as herein described).

In yet another aspect of the present invention, there is provided a method of manufacturing a topical formulation, the method including combining (i) comfrey or a comfrey-derived compound, or an analogue or derivative thereof (as herein described) with (ii) tannic acid, or an analogue or derivative thereof (as herein described).

The tannic acid (or analogue or derivative thereof) may be prepared as an at least partially purified compound during (e.g., at the same time as) preparation of the comfrey or comfrey-derived compound (or analogue or derivative thereof) or it may be prepared in isolation as an at least partially purified compound and subsequently combined with comfrey or the comfrey-derived compound (or analogue or derivative thereof), or a combination thereof. In a certain embodiment of the present invention, tannic acid is prepared as an at least partially purified compound and subsequently combined with comfrey or a comfrey-derived compound (or analogue or derivative thereof).

Methods of Prophylaxis and Treatment

In another aspect of the present invention, there is provided a method for the prophylactic or therapeutic treatment of an inflammatory and/or degenerative condition, wherein the method includes applying a topical formulation including (i) comfrey, or a comfrey-derived compound, or an analogue or derivative thereof, and a penetration, to a subject in need thereof and to an area affected by inflammation and/or degeneration or to an area expected of becoming affected by inflammation and/or degeneration, and optionally applying tannic acid to that area.

In yet another aspect of the present invention, there is provided a method for the prophylactic or therapeutic treatment of an inflammatory and/or degenerative condition, wherein the method includes applying a topical formulation including comfrey, a comfrey-derived compound, or an analogue or derivative thereof, and tannic acid, or an analogue or derivative thereof, to a subject in need thereof and to an area affected by inflammation and/or degeneration or to an area expected of becoming affected by inflammation and/or degeneration, and optionally applying a penetration enhancer to that area.

Whilst the active ingredients (e.g., penetration enhancer, comfrey, comfrey-derived compound, tannic acid, and analogues and derivatives thereof) may be applied to the subject in a single topical formulation according to the present invention, it would be appreciated that they may also be applied separately and in any given order.

Thus, in another embodiment of the present invention, there is provided a method for the prophylactic or therapeutic treatment of an inflammatory and/or degenerative condition, wherein the method includes applying, to a subject in need thereof and to an area affected by inflammation and/or degeneration or to an area expected of becoming affected by inflammation and/or degeneration, (i) comfrey or a comfrey-derived compound, or an analogue or derivative thereof, and (ii) tannic acid, or an analogue or derivative thereof, and optionally applying a penetration enhancer to the area.

In yet another embodiment of the present invention, there is provided a method for the prophylactic or therapeutic treatment of an inflammatory and/or degenerative condition, wherein the method includes applying, to a subject in need thereof and to an area affected by inflammation and/or degeneration or to an area expected of becoming affected by inflammation and/or degeneration, (i) comfrey or a comfrey-derived compound, or an analogue or derivative thereof, and (ii) a penetration enhancer, and optionally applying to the area tannic acid, or an analogue or derivative thereof.

The method of applying the active ingredients separately or as combined components in the topical formulation of the present invention will typically involve the application to an area affected by inflammation and/or degeneration (or an area expected to become affected by inflammation and/or degeneration), or to an area affected (or expected to become affected) by pain, swelling, stiffness and/or lack of mobility associated with said inflammation and/or degeneration. In a certain embodiment, the active ingredients (e.g., penetration enhancer, comfrey, comfrey-derived compound, tannic acid, etc) are applied to an area that surrounds the affected site (or to an area expected of becoming affected).

For instance, the active ingredients (e.g., penetration enhancer, comfrey, comfrey-derived compound, tannic acid, etc) may be applied separately, or as combined components in the topical formulation of the present invention, to an area that is all around the affected area or expected area of inflammation and/or degeneration. Where the topical formulation is a cream, gel, ointment or lotion, it may be spread on the body surface and gently rubbed in.

The dose regimen will depend on a number of factors that may readily be determined, such as the extent of inflammation and/or degeneration (or pain, swelling, stiffness and/or lack of mobility associated with said inflammation and/or degeneration) and the responsiveness of the inflammation, degeneration, pain, swelling, stiffness and/or lack of mobility to treatment, but will normally be one or more doses per day, with a course of treatment lasting from several days to several months, or until a cure is effected or a significant diminution in the extent of the inflammation, degeneration, pain, swelling, stiffness and/or lack of mobility experienced by the subject. One of ordinary skill may readily determine optimum dosages, dosing methodologies and repetition rates. In a certain embodiment, it is contemplated that the topical formulation will be applied one to five times daily. A suitable course of treatment or prophylaxis may be from about 1 to about 100 days. In another embodiment, a suitable course of treatment is 3 to 4 applications per day over a period of about 15 to about 90 days In another aspect of the present invention, there is provided a use of the topical formulation as herein described in the manufacture of a medicament for the prophylactic or therapeutic treatment of an inflammatory and/or degenerative condition, wherein the treatment includes applying an amount of said topical formulation to a subject in need thereof and to an area affected by inflammation and/or degeneration or to an area expected of becoming affected by inflammation and/or degeneration.

Types of inflammatory and/or degenerative conditions applicable to the methods and uses of the present invention include, but are not limited to, rheumatoid arthritis, septic arthritis, gout, pseudogout, juvenile arthritis, Still's disease, cervical spondylitis, lumbar spondylitis, frozen shoulder, calcaneal spurs, psoriatic arthritis, ankylosing spondylitis and osteoarthritis.

In a certain embodiment of the present invention, the subject is human. However, the methods of prophylactic or therapeutic treatment in accordance with the present invention may also be applicable to non-human subjects that are susceptible to inflammatory and/or degenerative conditions, including, but not limited to, horses, dogs, cats, rabbits and bovine.

Kits

In yet another aspect of the present invention, there is provided a kit, wherein the kit includes, in two or more containers, (i) a penetration enhancer (as herein described) and (ii) comfrey or a comfrey-derived compound, or an analogue or derivative thereof (as herein described), or (iii) any combination thereof. The kit may optionally include tannic acid, or an analogue or derivative thereof (as herein described), in a separate container or in combination with the penetration enhancer or in combination with comfrey or a comfrey-derived compound, or an analogue or derivative thereof.

In yet another aspect of the present invention, there is provided a kit, wherein the kit includes, in two or more containers, (i) tannic acid or an analogue or derivative thereof (as herein described) and (ii) comfrey or a comfrey-derived compound or an analogue or derivative thereof (as herein described), or (iii) any combination thereof. The kit may optionally include a penetration enhancer (as herein described) in a separate container or in combination with tannic acid (or an analogue or derivative thereof), or in combination with comfrey or a comfrey-derived compound (or an analogue or derivative thereof), as herein described.

In a further aspect, there is provided a kit including a container having a topical formulation according to the present invention, as herein described.

The kits according to the present invention may further include written instructions as to the use of the components in the prophylactic or therapeutic treatment of an inflammatory and/or degenerative condition, as herein described.

The discussion of documents, acts, materials, devices, articles and the like is included in this specification solely for the purpose of providing a context for the present invention. It is not suggested or represented that any or all of these matters formed part of the prior art base or were common general knowledge in the field relevant to the present invention before the priority date of each claim of this application.

Finally it is to be understood that various other modifications and/or alterations may be made without departing from the spirit of the present invention as outlined herein.

Future patent applications may be filed on the basis of or claiming priority from the present application.

Topical formulations according to certain embodiments of the present invention and procedures that may be used in the manufacture of the topical formulation according to certain embodiments of the present invention will now be described in the following examples. It should be understood, however, that the following description is illustrative only and should not be taken in any way as a restriction on the generality of the invention described above.

EXAMPLES

Example 1

Manufacturing Process for a Topical Cream Formulation

Materials

During the manufacturing process, stainless steel material of 305 grade or better is used in the manufacturing process. Also, tygon or similar grade tubing is used for the transfer of materials. A Waukesha (or a similar positive-displacement pump) was used for material transfer. A lightning-type variable speed mixer, a side-sweep mixer and an in-line homogenizer were also used in the following manufacturing process. The process tanks and mixing tanks were jacketed, as both heating and cooling is required for during the manufacturing process.

Cleaning and Sanitizing

Prior to commencement, all parts coming into contact with the final formulation (or intermediates thereof) are thoroughly cleaned with a suitable cleanser, rinsed and properly sanitized prior to use.

A. Main Mix Tank

Into the main mix tank, weigh in 50% of total batch weight water and add DMDM Hydantoin and glycerin. Begin mixing the ingredients at medium speed, then begin to heat the water. Slowly introduce tannic acid and the Ashwagantha extract, comfrey extract, methyl paraben and continue to mix. Heat the mixture to, and maintain the temperature at approximately 75° C.

B. Xanthan Gum Solution

In a small container, weigh in balance of the water (50%) and create a vortex using a high-speed lighting mixer. Slowly begin to sprinkle in the Xanthan gum and mix until completely hydrated, avoid lumping or fish eyes.

C. Oil Phase Mix Tank

In an oil-phase mix tank, weigh in castor oil, cylomethicone, dimethicone, cetyl alcohol, Arlacel 165, propyl paraben and olive oil. Begin heating the mixture to a temperature of 75° C. and maintain this temperature while mixing until the solution becomes uniform and clear.

D. Alcohol Tank

In a small tank, weigh in SD 40 Alcohol over a mixer at a slow speed (use an explosion proof mixer or an air mixer). Weigh in menthol, eucalyptus oil and lemon oil. Mix until the solution becomes clear and uniform and all of the menthol crystals have completely dissolved.

E. Propylene Glycol Tank

In a small tank, weigh in propylene glycol, pharmasolve (1-methylpyrrolidinone), frankincense (Boswellein) extract and cosmoperine. Warm the solution gently while mixing, heating to 55° C., but do not overheat. Continue mixing until the solution becomes clear and uniform.

Transfer the contents of the Propylene Glycol Tank (step E) into the Alcohol Tank (step D) and mix for approximately 5 to 10 minutes until the solution is uniform and clear.

F. Final Preparation

Transfer the contents of the Oil Phase Mix Tank (step C) into the Main Mix Tank (step A) and mix for approximately 10 to 15 minutes and or until uniform. When the Xanthan Gum Solution (step B) is completely hydrated, transfer it to the Main Mix Tank and mix for approximately 10 to 15 minutes or until homogeneous. Then, transfer the contents of the Alcohol Tank into the Main Mix Tank slowly, avoid pooling of solution, while mixing thoroughly for approximately 15 to 20 minutes until the solution is uniform and clear. Pass the entire batch solution through an in-line homogenizer as many times as required.

Example 2

Topical Gel Formulation

| Ingredient | % w/w |
| --- | --- |
| *Aloe Barbadensis* Leaf Juice | 52.1 |
| Tannic Acid | 15.0 |
| Comfrey Extract | 10.0 |
| Glycerin | 10.0 |
| Castor Oil | 10.0 |
| Xanthan Gum | 2.0 |
| Potassium Iodide | 0.2 |
| *Citrus Aurantium Dulsis* Seed Extract | 0.2 |
| Lavender Oil | 0.2 |
| *Eucalyptus* Oil | 0.2 |
| Ashwagandha Root Powder | 0.1 |
| Devils Claw Rhizome Extract Powder | 0.1 |
| *Epimedium* Leaf Extract Powder | 0.1 |
| Kelp *Laminaria* | 0.1 |

Example 3

Topical Drug Formulation

| Ingredient | % w/w. |
| --- | --- |
| Rosemarinic acid | 1.00 |
| Tannic acid | 10.00 |
| Tetra Hydro curcuminoid (THC) | 1.00 |
| Glycerine | 5.00 |
| Allantoin | 0.50 |
| Cetyl Alcohol | 4.00 |
| Arlacel 165 | 4.00 |
| castor oil | 5.00 |
| Eucalyptol | 4.00 |
| Dimethicone | 2.00 |
| Lecithin | 1.00 |
| Tetra hydropiperine (THP) | 0.25 |
| Tocopherol Polyethylene Glycol 100 succinate | 2.00 |
| Oleic Acid | 2.00 |
| Linolenic Acid | 2.00 |
| Propylene Glycol | 5.00 |
| Methyl Paraben | 0.20 |
| Propyl Paraben | 0.10 |
| DMDM Hydantoin | 0.20 |
| water | 50.75 |
| Total | 100.00 |

Water may also be replaced by or supplemented with Aloe juice.

Example 4

Topical Cream Formulation A

| Ingredient | % w/w |
| --- | --- |
| Ashwagandha (extract) | 3.00 |
| Castor oil | 1.00 |
| Comfrey (extract) | 20.00 |
| Frankincense (extract) | 2.00 |
| Glycerin | 2.00 |
| Tannic acid | 10.00 |
| Water | 26.40 |
| Borage oil | 2.00 |
| *Eucalyptus* oil | 4.00 |
| Cosmoperine | 0.30 |
| SD 40 Alcohol | 5.00 |
| Cyclomethicone | 2.00 |
| Dimethicone | 2.00 |
| Pharmasolve | 2.00 |
| Cetyl Alcohol | 5.00 |
| Arlacel 165 | 5.00 |
| Kelcoloid HVF | 0.75 |
| Propylene Glycol | 2.00 |
| Menthol | 4.00 |
| Methyl Paraben | 0.20 |
| Propyl Paraben | 0.10 |
| DMDM Hydantoin | 0.25 |
| Lemon oil | 1.00 |
| Total | 100.00 |

Example 5

Topical Cream Formulation B

| Ingredient | % w/w |
| --- | --- |
| Ashwagandha (extract) | 1.50 |
| Castor oil | 1.00 |
| Comfrey (extract) | 2.00 |
| Boswellein | 1.00 |
| Glycerin | 2.00 |
| Tannic acid | 8.00 |
| Allantoin | 0.50 |
| *Aloe vera* juice | 46.70 |
| Olive oil | 2.00 |
| *Eucalyptus* oil | 4.00 |
| Tetra hydro Piperine (THP) | 0.25 |
| SD 40 Alcohol | 8.00 |
| Cyclomethicone | 1.00 |
| Dimethicone | 1.00 |
| Methyl Pyrrolidone | 1.50 |
| Cetyl Alcohol | 4.00 |
| Arlacel 165 | 4.00 |
| Xanthan gum | 1.00 |
| Propylene Glycol | 5.00 |
| Menthol | 4.00 |
| Methyl Paraben | 0.20 |
| Propyl Paraben | 0.10 |
| DMDM Hydantoin | 0.25 |
| Lemon oil | 1.00 |
| Total | 100.00 |

Example 6

Topical Cream Formulation C

| Ingredient | % w/w |
| --- | --- |
| Ashwagandha (extract) | 1.50 |
| Castor oil | 1.00 |
| Comfrey (extract) | 2.00 |
| Boswellein | 1.00 |
| Glycerin | 2.00 |
| Tannic acid | 8.00 |
| Allantoin | 0.50 |
| Water | 27.15 |
| Olive oil | 2.00 |
| *Eucalyptus* oil | 4.00 |
| Tetra hydro Piperine (THP) | 0.30 |
| SD 40 Alcohol | 4.00 |
| Cyclomethicone | 1.00 |
| Dimethicone | 1.00 |
| Methyl Pyrrolidone | 2.00 |
| Cetyl Alcohol | 4.00 |
| Arlacel 165 | 4.00 |
| Xanthan gum 4% | 25.00 |
| Propylene Glycol | 4.00 |
| Menthol | 4.00 |
| Methyl Paraben | 0.20 |
| Propyl Paraben | 0.10 |
| DMDM Hydantoin | 0.25 |
| Lemon oil | 1.00 |
| Total | 100.00 |

Example 7

Topical Cream Formulation D

| Ingredient | % w/w |
| --- | --- |
| Ashwagandha (extract) | 1.50 |
| Castor oil | 1.00 |
| Comfrey (extract) | 10.00 |
| Boswellein | 1.00 |
| Glycerin | 2.00 |
| Tannic acid | 10.00 |
| Water | 40.15 |
| Olive oil | 2.00 |
| *Eucalyptus* oil | 4.00 |
| Tetra hydropiperine (THP) | 0.30 |
| SD 40 Alcohol | 4.00 |
| Cyclomethicone | 2.00 |
| Dimethicone | 1.00 |
| Methyl Pyrrolidone | 2.00 |
| Cetyl Alcohol | 4.50 |
| Arlacel 165 | 4.50 |
| Propylene Glycol Alginate | 0.50 |
| Propylene Glycol | 4.00 |
| Menthol | 4.00 |
| Methyl Paraben | 0.20 |
| Propyl Paraben | 0.10 |
| DMDM Hydantoin | 0.25 |
| Lemon oil | 1.00 |
| Total | 100.00 |

Example 8

Topical Cream Formulation E

| Ingredient | % w/w |
| --- | --- |
| Ashwagandha (extract) | 1.50 |
| Castor oil | 1.00 |
| Comfrey (extract) | 2.00 |
| Frankincense (extract) | 1.00 |
| Glycerin | 2.00 |
| Tannic acid | 10.00 |
| Olive oil | 2.00 |
| *Eucalyptus* oil | 4.00 |
| Cosmoperine | 0.25 |
| SD 40 Alcohol | 4.00 |
| Cyclomethicone | 1.00 |
| Dimethicone | 1.00 |
| Pharmasolve | 1.50 |
| Cetyl Alcohol | 5.00 |
| Arlacel 165 | 5.00 |
| Xanthan gum | 1.00 |
| Propylene Glycol | 4.00 |
| Menthol | 4.00 |
| Methyl Paraben | 0.20 |
| Propyl Paraben | 0.10 |
| DMDM Hydantoin | 0.25 |
| Lemon oil | 1.00 |
| Water | 48.20 |
| Total | 100.00 |

Example 9

Topical Cream Formulation F

| Ingredient | % w/w |
| --- | --- |
| Ashwagandha (extract) | 1.50 |
| Castor oil | 1.00 |
| Comfrey (extract) | 20.00 |
| Frankincense (extract) | 1.00 |
| Glycerin | 2.00 |
| Tannic acid | 10.00 |
| Olive oil | 2.00 |
| *Eucalyptus* oil | 4.00 |
| Cosmoperine | 0.25 |
| SD 40 Alcohol | 4.00 |
| Cyclomethicone | 1.00 |
| Dimethicone | 1.00 |
| Pharmasolve | 1.50 |
| Cetyl Alcohol | 5.00 |
| Arlacel 165 | 5.00 |
| Allantoin | 1.00 |
| Xanthan gum | 1.00 |
| Propylene Glycol | 4.00 |
| Menthol | 4.00 |
| Methyl Paraben | 0.20 |
| Propyl Paraben | 0.10 |
| DMDM Hydantoin | 0.25 |
| Lemon oil | 1.00 |
| *Aloe Vera* Juice | 29.20 |
| Total | 100.00 |

Example 10

Topical Cream Formulation G

| Ingredient | % w/w |
| --- | --- |
| Ashwagandha (extract) | 1.50 |
| Castor oil | 1.00 |
| Comfrey (extract) | 20.00 |
| Boswellein (extract) | 1.00 |
| Glycerin 99% | 2.00 |
| Tannic acid | 10.00 |
| Water | 5.00 |
| Xanthan Gum | 1.00 |
| Olive oil | 4.00 |
| *Eucalyptus Globulas* oil | 4.00 |
| Cosmoperine (THP) | 0.25 |
| SD-40 Alcohol | 4.00 |
| Dow Corning 345 | 1.00 |
| Dow Corning 200 350 cts | 1.00 |
| 1-Methyl 2-Pyrrolidinone | 1.50 |
| Cetyl Alcohol | 4.50 |
| ARLACEL165 | 4.50 |
| Propylene Glycol | 4.00 |
| Methyl Paraben | 0.20 |
| Propyl Paraben | 0.10 |
| DMDM Hydantoin | 0.25 |
| Lemon oil | 1.00 |
| Extract Complex I | 0.30 |
| Oil Complex I | 0.30 |
| Alovera Juice | 27.60 |
| TOTAL | 100.00 |

Extract Complex I includes Chamomile, Willow Bark, Arnica, Calendula, Yarrow, Licorice, Root, Oregano, Marjoram and St. John's wort. Oil Complex I includes Lemon Balm, Grapefruit (white), Blue Cypress, Rosemary Oil, Sage and Lemon Myrtle.

Example 11

Topical Cream Formulation H

| Ingredient | % w/w |
| --- | --- |
| Ashwagandha (extract) | 1.50 |
| Castor oil | 1.00 |
| Comfrey (extract) | 10.00 |
| Boswellein (extract) | 1.00 |
| Glycerin 99% | 2.00 |
| Tannic acid | 10.00 |
| Water | 15.00 |
| Xanthan Gum | 1.00 |
| Olive oil | 4.00 |
| *Eucalyptus Globulas* oil | 4.00 |
| Cosmoperine (THP) | 0.25 |
| SD-40 Alcohol | 4.00 |
| Dow Corning 345 | 1.00 |
| Dow Corning 200 350 cts | 1.00 |
| 1-Methyl 2-Pyrrolidinone | 1.50 |
| Cetyl Alcohol | 4.50 |
| ARLACEL165 | 4.50 |
| Propylene Glycol | 4.00 |
| Methyl Paraben | 0.20 |
| Propyl Paraben | 0.10 |
| DMDM Hydantoin | 0.25 |
| Lemon oil | 1.00 |
| Extract Complex I | 0.30 |
| Oil Complex I | 0.30 |
| Alovera Juice | 27.60 |
| TOTAL | 100.00 |

Extract Complex I includes Chamomile, Willow Bark, Arnica, Calendula, Yarrow, Licorice, Root, Oregano, Marjoram and St. John's wort. Oil Complex I includes Lemon Balm, Grapefruit (white), Blue Cypress, Rosemary Oil, Sage and Lemon Myrtle.

Example 12

Manufacturing Process for a Topical Cream Formulation—A

Materials

During the manufacturing process, stainless steel material of 305 grade or better is used in the manufacturing process. Also, tygon or similar grade tubing is used for the transfer of materials. A Waukesha (or a similar positive-displacement pump) was used for material transfer. A lightning-type variable speed mixer, a side-sweep mixer and an in-line homogenizer were also used in the following manufacturing process. The process tanks and mixing tanks were jacketed, as both heating and cooling is required for during the manufacturing process.

Cleaning and Sanitizing

Prior to commencement, all parts coming into contact with the final formulation (or intermediates thereof) are thoroughly cleaned with a suitable cleanser, rinsed and properly sanitized prior to use.

Process

Comfrey crude is passed along a conveyor, cooled using a controlled amount of liquid nitrogen, and passed through a grinding mill to generate, for example, finely ground particles.

After the Comfrey is ground, it can be used in the topical formulation using, for example, the following manufacturing process:

A. Main Mix Tank

Into the main mix tank, weigh in 50% of total batch weight water and add DMDM Hydantoin and glycerin. Begin mixing the ingredients at medium speed, then begin to heat the water. Slowly introduce tannic acid and the Ashwagantha extract, comfrey extract, methyl paraben and continue to mix. Heat the mixture to, and maintain the temperature at, 75° C.

B. Xanthan Gum Solution

In a small container, weigh in balance of the water (50%) and create a vortex using a high-speed lighting mixer. Slowly begin to sprinkle in the Xanthan gum and mix until completely hydrated, avoid lumping or fish eyes.

C. Oil Phase Mix Tank

In an oil-phase mix tank, weigh in castor oil, cetyl alcohol, Arlacel 165, propyl paraben and olive oil. Begin heating the mixture to a temperature of 75° C. and maintain this temperature while mixing until the solution becomes uniform and clear.

D. Alcohol Tank

In a small tank, weigh in SD 40 Alcohol over a mixer at a slow speed (use an explosion proof mixer or an air mixer). Weigh in menthol, eucalyptus oil and lemon oil. Mix until the solution becomes clear and uniform and all of the menthol crystals have completely dissolved.

E. Propylene Glycol Tank

In a small tank, weigh in propylene glycol, pharmasolve (1-methylpyrrolidinone), frankincense (Boswellein) extract and cosmoperine. Warm the solution gently while mixing, heating to 55° C., but do not overheat. Continue mixing until the solution becomes clear and uniform.

Transfer the contents of the Propylene Glycol Tank (step E) into the Alcohol Tank (step D) and mix for approximately 5 to 10 minutes until the solution is uniform and clear.

F. Final Preparation

Transfer the contents of the Oil Phase Mix Tank (step C) into the Main Mix Tank (step A) and mix for approximately 10 to 15 minutes and or until uniform. When the Xanthan Gum Solution (step B) is completely hydrated, transfer it to the Main Mix Tank and mix for approximately 10 to 15 minutes or until homogeneous. Then, transfer the contents of the Alcohol Tank into the Main Mix Tank slowly, avoid pooling of solution, while mixing thoroughly for approximately 15 to 20 minutes until the solution is uniform and clear. Pass the entire batch solution through an in-line homogenizer as many times as required.

Using a high-pressure homogenization process, the entire batch is passed through at a predetermined PSI (e.g., 5,000-15,000 pounds per square inch) for a single or double pass. A BBBI machine may be used, for example, to create a uniform, evenly distributed particle size to the topical cream formulation.

Example 13

Manufacturing Process for a Topical Cream Formulation—B

A. Main Mix Tank

Weigh in aloevera juice, add water and turn on lightning mixer or similar mixer to create vortex. Then add Ashwagantha powder extract and mix until dissolved. Slowly sprinkle in Xanthan gum and continue mixing until the solution is uniform to avoid lumps or fish eyes. Add glycerine, DMDM Hydantoin and heat the batch to approximately 70° C. and maintain at that temperature.

B. Oil Phase Mix Tank

In a suitable container, weigh in Dow Corning 200, Dow Corning 345, olive oil, castor oil, cetyl alcohol, Lipomulse 165 and propyl paraben and heat mixture to 75° C. until the mixture becomes clear and uniform. Transfer oil phase to the Main Mix Tank, continue mixing for 10 minutes or until the solution becomes homogeneous. Start cooling the batch to approximately 40° C.

C. Comfrey Extract Pre-Mix

In a separate container, weigh in Comfrey extract and mix to create vortex. Slowly sprinkle in tannic acid and mix until uniform to avoid lumps then set aside. At approximately 40° C., transfer the contents of the Comfrey Extract Pre-mix to the Main Mix Tank and continue mixing for approximately 10 minutes or until homogeneous.

C. Propylene Glycol-Boswellein Pre-Mix

In a suitable container, weigh in propylene glycol, 1-methyl 2-pyrrolidone and then add methyl paraben, cosmoperine (THP) and boswellein extract and warm the solution to 45° C. and mix until clear. Add eucalyptus globulus oil, SD-40 alcohol and mix until clear. Add lemon oil and continue to mix until clear and uniform. Transfer the content of propylene glycol-boswellein Pre-mix tank into the Main Mix tank and continue mixing until uniform and homogeneous. Add Extract Complex I and Oil Complex I into Main Mix tank and continue mixing for approximately 10 minutes.

C. Final Step

Homogenize the entire batch for approximately five to seven minutes or until cream appears smooth (for Lab Batch, use Homo Mixer using a medium screen size).

Example 14

Topical Cream Formulation I

| Ingredient | % w/w |
| --- | --- |
| Ashwagandha (extract) | 1.50 |
| Castor oil | 2.50 |
| Comfrey (crude powder), prepared in accordance with the process referred to in Example 12 above. | 5.00 |
| Glycerin | 2.50 |
| Kelp (extract) | 2.00 |
| Tannic Acid | 10.00 |
| Frankincense (extract) | 1.00 |
| Lemon (essential oil) | 1.00 |
| Cosmoperine (THP) | 0.25 |
| Menthol | 4.00 |
| Cetyl Alcohol | 4.00 |
| Arlacel165 | 4.00 |
| *Eucalyptus* oil | 4.00 |
| Xanthan Gum | 1.00 |
| Propylene Glycol | 2.00 |
| Methyl Paraben | 0.20 |
| Propyl Paraben | 0.10 |
| DMDM Hydantoin | 0.25 |
| SD 40 alcohol | 5.00 |
| Propylene glycol | 4.00 |
| olive oil | 2.00 |
| M. Pyrole | 1.50 |
| water | 42.20 |
| Total | 100.00 |

Example 15

Topical Drug Formulation J

| Ingredient | % w/w |
| --- | --- |
| Xanthan Gum | 1.00 |
| Rosemarinic acid | 0.14 |
| Tannic acid | 10.00 |
| Tetrahydro curcuminoid (THC) | 0.50 |
| Allantoin | 0.50 |
| Cetyl Alcohol | 4.00 |
| GMS Self Emulsifying | 4.00 |
| Eucalyptol | 5.00 |
| Dimethicone (Dow Corning 200) | 2.00 |
| SD 40 Alcohol | 5.00 |
| *M. Pyrrole* | 1.50 |
| Glycyrrhizic Acid Monoammonium salt | 0.29 |
| 18 beta Glycyrrhetinic Acid | 0.29 |
| Vitamin E TPGS | 2.00 |
| Oleic Acid | 5.00 |
| Propylene Glycol | 5.00 |
| Germaben II | 1.00 |
| Lemon Oil | 1.00 |
| water | 51.77 |
| Total | 100.00 |

Example 16

Treatment of Inflammatory and/or Degenerative Conditions

Patients with varying ailments associated with an inflammatory and/or degenerative condition were treated with a topical cream formulation according to the present invention.

Patient 1

At the commencement of treatment, this patient presented with osteoarthritis of the thumb. Prior to treatment, the patient experienced pain in the affected area, whose intensity was recorded as 5/10. After 4 weeks of treatment using the topical formulation according to the present invention, the patient experienced a marked reduction in pain in the affected area to a level of 1/10. The treatment was well tolerated and the patient did not report any adverse reaction to the treatment.

Patient 2

At the commencement of treatment, this patient presented with plantar fascitis/calcaneal heel spur. Prior to treatment, the patient experienced pain in the affected area, whose intensity was recorded as 8/10. After 4 weeks of treatment using the topical formulation according to the present invention, the patient experienced a marked reduction in pain in the affected area to a level of 3/10. This patient is continuing treatment.

Patient 3

At the commencement of treatment, this patient presented with osteoarthritis of the left elbow. Prior to treatment, the patient experienced pain in the affected area, whose intensity was recorded as 5/10. After 4 weeks of treatment using the topical formulation according to the present invention, the patient experienced a significant improvement and had no pain in the affected area (recorded level of pain at 4 weeks post-treatment: 0/10). The treatment was well tolerated and the patient did not report any adverse reaction to the treatment.

Patient 4

At the commencement of treatment, this patient presented with plantar fascitis/calcaneal heel spur. Prior to treatment, the patient experienced pain in the affected area, whose intensity was recorded as 7/10. After 4 weeks of treatment using the topical formulation according to the present invention, the patient experienced a marked reduction in pain in the affected area to a level of 3/10. This patient is continuing treatment.

Patient 5

At the commencement of treatment, this patient presented with osteoarthritis of the knee. Prior to treatment, the patient experienced pain in the affected area, whose intensity was recorded as 8/10. After 1 week of treatment using the topical formulation according to the present invention, the patient experienced a significant reduction in pain in the affected area to a level of 6/10. This patient is continuing treatment.

Patient 6

At the commencement of treatment, this patient presented with osteoarthritis of the right knee. Prior to treatment, the patient experienced severe pain in the affected area, whose intensity was recorded as 10/10. After 5 week of treatment using the topical formulation according to the present invention, the patient experienced a marked reduction in pain in the affected area to a level of 1/10. This patient is continuing treatment.

Patient 7

At the commencement of treatment, this patient presented with osteoarthritis of the fingers of the left and right hands. Prior to treatment, the patient experienced severe pain in the affected area, whose intensity was recorded as 10/10. Flexibility and mobility were also recorded using a score of 1 to 10, where 1 denotes minimum pain, flexibility or mobility and 10 denotes maximum pain, flexibility or mobility.

| DAY | | PAIN LEVEL (1-10) | FLEXIBILITY (1-10) | MOBILITY (1-10) |
| --- | --- | --- | --- | --- |
| 1 | | 8 | 8 | 8 |
| 10 | | 8 | 8 | 8 |
| 20 | (right hand) | 7 | 7 | 7 |
| | (left hand) | 6 | 6 | 6 |
| 30 | (left hand) | 5 | 5 | 5 |
| | (right hand) | 7 | 7 | 7 |
| 40 | (left hand) | 4 | 4 | 4 |
| | (right hand) | 6 | 6 | 6 |
| 50 | (left hand) | 2 | 2 | 2 |
| | (right hand) | 5 | 5 | 5 |
| 60 | (left hand) | 3 | 3 | 3 |
| | (right hand) | 5 | 5 | 5 |
| 70 | (left hand) | 2 | 2 | 2 |
| | (right hand) | 4 | 4 | 4 |

Example 17

Treatment of Inflammatory and/or Degenerative Conditions—Randomized Controlled Clinical Trial (I) Methodology A randomized controlled clinical trial of 5 different formulations was conducted with a cohort of patients presenting with arthritis. The formulations used in the study were as follows:

G1=20% Comfrey extract and tannic acid
G2=10% Comfrey extract and tannic acid
G3=Formulation without Comfrey extract
G4=Formulation without tannic acid
G5=Topical Drug Formulation J, as described in Example 15 above.

| Ingredient | % w/w Formulations | | | |
|---|---|---|---|---|
| | G1 | G2 | G3 | G4 |
| Ashwagandha (extract) | 1.50 | 1.50 | 1.50 | 1.50 |
| Castor oil | 1.00 | 1.00 | 1.00 | 1.00 |
| Comfrey, extract | 20.00 | 10.00 | 0.00 | 20.00 |
| Boswellein (extract) | 1.00 | 1.00 | 1.00 | 1.00 |
| Glycerin 99% | 2.00 | 2.00 | 2.00 | 2.00 |
| Tannic acid | 10.00 | 10.00 | 10.00 | 0.00 |
| Water | 4.70 | 14.70 | 24.70 | 14.70 |
| Xanthan Gum | 1.00 | 1.00 | 1.00 | 1.00 |
| Olive oil | 4.00 | 4.00 | 4.00 | 4.00 |
| *Eucalyptus Globulas* oil | 4.00 | 4.00 | 4.00 | 4.00 |
| Cosmoperine (THP) | 0.25 | 0.25 | 0.25 | 0.25 |
| SD-40 Alcohol | 4.00 | 4.00 | 4.00 | 4.00 |
| Dow Corning 345 | 1.00 | 1.00 | 1.00 | 1.00 |
| Dow Corning 200 350 cts | 1.00 | 1.00 | 1.00 | 1.00 |
| 1-Methyl 2-Pyrrolidinone | 1.50 | 1.50 | 1.50 | 1.50 |
| Cetyl Alcohol | 4.50 | 4.50 | 4.50 | 4.50 |
| ARLACEL165 | 4.50 | 4.50 | 4.50 | 4.50 |
| Propylene Glycol | 4.00 | 4.00 | 4.00 | 4.00 |
| Methyl Paraben | 0.20 | 0.20 | 0.20 | 0.20 |
| Propyl Paraben | 0.10 | 0.10 | 0.10 | 0.10 |
| DMDM Hydantoin | 0.25 | 0.25 | 0.25 | 0.25 |
| Lemon oil | 1.00 | 1.00 | 1.00 | 1.00 |
| Extract Complex I | 0.30 | 0.30 | 0.30 | 0.30 |
| Oil Complex I | 0.30 | 0.30 | 0.30 | 0.30 |
| Alovera Juice | 27.90 | 27.90 | 27.90 | 27.90 |
| TOTAL | 100.00 | 100.00 | 100.00 | 100.00 |

Analyses were performed using 2 different scoring systems: the Womac Osteoarthritis Index and the Numerical Rating Scale. The Womac Osteoarthritis Index is a tri-dimensional, disease-specific, self-administered, health status measure. It probes clinically-important symptoms in the areas of pain, stiffness and physical function in patients with osteoarthritis of the hip and/or knee. The Index consists of 24 questions (5 relating to pain, 2 relating to stiffness and 17 relating to physical function). It is sufficiently sensitive to detect clinically important changes in health status following a variety of interventions.

The Numerical Rating Scale is one of the most popular pain assessment tools in the art that assist patients to describe their pain. The pain scale is one tool commonly used to describe the intensity of the pain or how much pain the patient is feeling (the pain scales include the Numerical Rating Scale, the Visual Analog Scale, the Categorical Scale, and the Pain Faces Scale). On the Numerical Rating Scale, the person is asked to identify how much pain they are experiencing by choosing a number from 0 (no pain) to 10 (the worst pain imaginable). This scale is also used to rate their perception of ability to do activities.

The results represent data derived from a cohort of 30 patients.

(ii) Results—Womac Osteoarthritis Index

| Pain | Womac Mean Initial | Womac Mean 8 Week | Pre to 8 Week Gain | Rank of Formula based on Pre- to 8 Week Gain | % of Change | Rank based on % of Change |
|---|---|---|---|---|---|---|
| G1 | 257.33 | 81.00 | 176.33 | 1 | 68.52% | 1 |
| G2 | 222.58 | 171.25 | 51.33 | 2 | 23.06% | 5 |
| G3 | 252.40 | 170.00 | 82.40 | 4 | 32.65% | 4 |
| G4 | 241.15 | 154.40 | 86.75 | 5 | 35.97% | 3 |
| G5 | 253.86 | 153.17 | 100.69 | 3 | 39.66% | 2 |

| | Pre | 8 Week | Pre to 8 Week Gain | Rank of Formula based on Pre- to 8 Week Gain | % of Change | Rank based on % of Change |
|---|---|---|---|---|---|---|
| Stiffness | | | | | | |
| G1 | 104.17 | 44.29 | 59.88 | 3 | 57.48% | 2 |
| G2 | 120.92 | 45.50 | 75.42 | 1 | 62.37% | 1 |
| G3 | 104.87 | 82.50 | 22.37 | 5 | 21.33% | 5 |
| G4 | 93.69 | 64.40 | 29.29 | 4 | 31.26% | 4 |
| G5 | 115.21 | 53.17 | 62.05 | 2 | 53.85% | 3 |
| Activities | | | | | | |
| G1 | 944.08 | 270.42 | 673.66 | 1 | 71.36% | 1 |
| G2 | 943.17 | 655.25 | 287.92 | 3 | 30.53% | 5 |
| G3 | 795.47 | 521.00 | 274.47 | 4 | 34.50% | 4 |
| G4 | 765.92 | 489.60 | 276.32 | 5 | 36.08% | 3 |
| G5 | 953.29 | 486.33 | 466.96 | 2 | 48.98% | 2 |

Based on the analysis of the Womac Osteoarthritis Index findings after 8 weeks of treatment, the results show that formula G1 (20% comfrey with tannic acid) was the most effective for pain, formula G2 (10% comfrey with tannic acid) was the most effective for stiffness, and formula G1 (20% comfrey with tannic acid) was the most effective in alleviating difficulty in performing daily activities. Furthermore, formula G2 (10% comfrey with tannic acid) was found to be the second most effective formulation for pain, while formula G5 (the topical drug formulation) was found to be the second most effective formulation for stiffness and for alleviating difficulty in performing daily activities. The three formulations that included a combination of comfrey and tannic acid showed superiority over formulations with only comfrey or tannic acid alone. These results demonstrate a synergistic effect between comfrey and tannic acid in comparison to individual compounds in the treatment of conditions such as arthritis. This is based on 8 weeks of using the formula (The study test period).

(ii) Results—The Numerical Rating Scale

| Historical Pain | NRS Mean Pre- | NRS Mean 8 Week | Pre- to 8 Week Gain | Rank based on Pre to 8 Week Gain | % of Change | Rank based on % of Change |
|---|---|---|---|---|---|---|
| G1 | 6.29 | 3.33 | 2.96 | 1 | 47.02% | 1 |
| G2 | 6.71 | 4.10 | 2.61 | 2 | 38.88% | 2 |
| G3 | 6.17 | 4.20 | 1.97 | 4 | 31.89% | 4 |
| G4 | 6.19 | 4.80 | 1.39 | 5 | 22.48% | 5 |
| G5 | 7.11 | 4.50 | 2.61 | 3 | 36.68% | 3 |

| | Pre | 8 Wk | Pre to 8 Week Gain | Rank based on Pre to 8 Week Gain | % of Change | Rank based on % of Change |
|---|---|---|---|---|---|---|
| 48 Hr Pain | | | | | | |
| G1 | 6.75 | 3.33 | 3.42 | 1 | 50.62% | 1 |
| G2 | 7.17 | 4.10 | 3.07 | 2 | 42.79% | 2 |
| G3 | 7.00 | 4.20 | 2.80 | 3 | 40.00% | 3 |
| G4 | 5.92 | 4.80 | 1.12 | 5 | 18.96% | 5 |
| G5 | 6.00 | 4.50 | 1.50 | 4 | 25.00% | 4 |
| Ability | | | | | | |
| G1 | 6.29 | 3.00 | 3.29 | 1 | 52.32% | 1 |
| G2 | 6.67 | 4.00 | 2.67 | 2 | 40.00% | 2 |
| G3 | 6.53 | 4.80 | 1.73 | 3 | 26.53% | 3 |
| G4 | 6.00 | 4.80 | 1.20 | 4 | 20.00% | 4 |
| G5 | 5.79 | 5.00 | 0.79 | 5 | 13.58% | 5 |

These figures are based on a Numerical Rating Scale used by each subject at the initiation of the study and after 8 weeks of treatment. The historical pain is based on a Numerical Rating Scale of the patient's pain over the past 30 days as opposed to the last 48 hours.

Based on the analysis of the Numerical Rating Scale after 8 weeks of treatment, the results show that formula al (20% comfrey with tannic acid) was the most effective for pain relief based on past 30 days, formula al (20% comfrey with tannic acid) was the most effective for pain relief based on last 48 hours, and formula al (20% comfrey with tannic acid) was the most effective in alleviating difficulty in performing daily activities. Furthermore, formula G2 (10% comfrey with tannic acid) was found to be second most effective formulation in each category (i.e., pain, stiffness and activity). These data demonstrate a synergistic effect between comfrey and tannic acid in comparison to comfrey and tannic acid alone.

Both the Womac Osteoarthritis Index and the Numerical Rating Scale demonstrate that formulations including comfrey and tannic acid in combination are more effective than formulations with either comfrey or tannic acid alone.

The invention claimed is:

1. A topical formulation including a synergistic combination of active agents capable of providing a synergistic improvement in joint stiffness in patients with osteoarthritis, wherein the synergistic combination of active agents consists essentially of (i) a comfrey extract and (ii) tannic acid, wherein the comfrey extract is a comfrey leaf extract, a comfrey root extract or a combination thereof, wherein the comfrey extract is at least 0.5% to about 40% of the total weight of the topical formulation, and wherein the tannic acid is included in an amount that is at least about 2% to 20% of the total weight of the topical formulation, and wherein the synergistic combination of the active agents of comfrey to tannic acid is from 2:1 to 1:1 by weight.

2. The topical formulation according to claim 1, wherein the tannic acid is a substantially pure, pharmaceutical grade tannic acid.

3. The topical formulation according to claim 1, further comprising eucalyptus oil.

4. The topical formulation according to claim 1, further comprising menthol.

* * * * *